US009557270B2

(12) United States Patent
Tokhtuev et al.

(10) Patent No.: US 9,557,270 B2
(45) Date of Patent: Jan. 31, 2017

(54) MULTI-CHANNEL FLUOROMETRIC SENSOR AND METHOD OF USING SAME

(71) Applicant: Ecolab USA Inc., St. Paul, MN (US)

(72) Inventors: Eugene Tokhtuev, Duluth, MN (US); Anatoly Skirda, Hermantown, MN (US); William M. Christensen, Hibbing, MN (US)

(73) Assignee: Ecolab USA Inc., St. Paul, MN (US)

( * ) Notice: Subject to any disclaimer, the term of this patent is extended or adjusted under 35 U.S.C. 154(b) by 6 days.

(21) Appl. No.: 14/637,576

(22) Filed: Mar. 4, 2015

(65) Prior Publication Data
US 2016/0258870 A1 Sep. 8, 2016

(51) Int. Cl.
*G01N 21/64* (2006.01)
*G01N 21/51* (2006.01)

(52) U.S. Cl.
CPC ............ *G01N 21/645* (2013.01); *G01N 21/51* (2013.01); *G01N 21/6428* (2013.01); *G01N 2021/6439* (2013.01)

(58) Field of Classification Search
CPC ............ G01N 2021/6439; G01N 21/51; G01N 21/6428; G01N 21/645
See application file for complete search history.

(56) References Cited

U.S. PATENT DOCUMENTS

| | | | |
|---|---|---|---|
| 6,089,242 A | 7/2000 | Buck | |
| 6,369,894 B1 | 4/2002 | Rasimas et al. | |
| 6,423,152 B1 | 7/2002 | Landaas | |
| 6,767,408 B2 | 7/2004 | Kenowski et al. | |
| 7,060,136 B1 | 6/2006 | Zeiher et al. | |
| 7,099,012 B1 | 8/2006 | Crawford et al. | |
| 7,247,210 B2 | 7/2007 | Staub et al. | |
| 7,614,410 B2 | 11/2009 | Kenowski et al. | |
| 7,989,780 B2 | 8/2011 | Tokhtuev et al. | |
| 8,248,611 B2 | 8/2012 | Christensen et al. | |
| 8,269,193 B2 | 9/2012 | Christensen et al. | |
| 8,373,140 B2 | 2/2013 | Tokhtuev et al. | |
| 2004/0057050 A1 | 3/2004 | Beck et al. | |
| 2006/0286676 A1 | 12/2006 | Van Camp et al. | |

(Continued)

OTHER PUBLICATIONS

Banks, Rodney H. et al., U.S. Appl. No. 14/039,683, entitled "Multi-Channel Fluorometric Sensor and Method of Using Same," filed Sep. 27, 2013, 69 pages.

(Continued)

*Primary Examiner* — Mark R Gaworecki
(74) *Attorney, Agent, or Firm* — Fredrikson & Byron, P.A.

(57) ABSTRACT

An optical sensor can include first and second optical emitters configured to emit light into a fluid sample via an optical pathway. Light from the emitters can cause fluorescence from the sample and/or scatter off of the sample. Scattered and fluoresced light can be received by an optical detector in the sensor via the optical pathway, and used to determine at least one characteristic of the fluid sample. A second optical detector can provide reference measurements of the amount of light emitted to the sample. The second optical emitter and second optical detector can be included in an optical emitter assembly removably disposed in the optical pathway of the optical sensor such that the second optical emitter emits light into the optical pathway toward a fluid sample.

25 Claims, 16 Drawing Sheets

(56) References Cited

U.S. PATENT DOCUMENTS

| | | | |
|---|---|---|---|
| 2008/0002180 A1* | 1/2008 | Gigioli | G01J 3/02 |
| | | | 356/51 |
| 2008/0186479 A1 | 8/2008 | Swalwell et al. | |
| 2010/0048730 A1 | 2/2010 | Li et al. | |
| 2010/0053614 A1 | 3/2010 | Jeys et al. | |
| 2011/0197920 A1 | 8/2011 | Kenowski et al. | |
| 2011/0246118 A1* | 10/2011 | Tokhtuev | G01N 21/274 |
| | | | 702/104 |
| 2012/0062881 A1 | 3/2012 | Sakagami et al. | |

OTHER PUBLICATIONS

International Search Report and Written Opinion for International Application No. PCT/US2016/020963; Date of Mailing: Jun. 20, 2016, 10 pages.

\* cited by examiner

MULTI-CHANNEL FLUOROMETRIC SENSOR AND METHOD OF USING SAME

TECHNICAL FIELD

This disclosure relates to optical measuring devices and, more particularly, to fluorometers for monitoring the concentration of one or more substances in a sample.

BACKGROUND

In cleaning and antimicrobial operations, commercial users (e.g., restaurants, hotels, food and beverage plants, grocery stores, etc.) rely upon the concentration of a cleaning or antimicrobial product to make the product work effectively. Failure of a cleaning or antimicrobial product to work effectively (for example due to concentration issues) can cause a commercial user to perceive the product as lower quality. End consumers may also perceive the commercial provider of such products as providing inferior services. In addition, commercial users may be investigated and/or sanctioned by government regulatory and health agencies. Accordingly, there is a need for a system that can monitor the characteristics of fluid solutions, e.g., to determine if the concentration of a product is within a specified concentration range. The same may be true for other applications, such as commercial and industrial water treatment, pest control, beverage and bottling operations, oil and gas refining and processing operations, and the like.

One method of monitoring the concentration of a product relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence.

Generally, fluorometric spectroscopy requires directing light from a source of radiant light to a sample and then receiving light from the sample at a detector. In order to do so, the source and detector must be in optical communication with the sample. In existing systems, providing optical access to the sample can be a costly process requiring significant modification to the system and significant downtime to perform such modification.

SUMMARY

In general, this disclosure is related to fluorometers and techniques for monitoring fluid samples. In some examples, a fluorometer according to the disclosure includes a first optical emitter configured to generate fluorescent emissions in a fluid sample under analysis and a second optical emitter configured to emit light to measure an amount of scattering in the fluid sample under analysis. The fluorometer may also include at least one detector that receives fluorescent light emitted from the fluid sample and/or light scattered from the fluid sample. During operation, the detector can detect an amount of fluorescent light emitted from the fluid sample under analysis and the fluorometer can then determine, based on the fluorescent light, a concentration of a fluorescing species in the fluid sample. The fluorometer can also detect an amount of light scattered by the fluid sample under analysis and determine, based on the scattered light, other properties of the fluid sample under analysis. For example, the fluorometer may determine a concentration of a non-fluorescing species in the fluid sample under analysis. As another example, the fluorometer may adjust the amount of fluorescent light detected based on the light scattering information, e.g., to account for the effect of fluid turbidity on the measured intensity of the fluorescent emissions.

To help provide a compact fluorometer design that is easy to install and that resists fouling, the fluorometer may be configured with a single optical lens through which light is emitted into and received from the fluid sample under analysis. The fluorometer may include a housing that contains the first optical emitter, the second optical emitter, and at least one detector. The first optical emitter, the second optical emitter, and the at least one detector may be arranged within the housing so that all the components are in optical communication with the single optical lens (e.g., can direct light through and/or receive light from the optical lens). By configuring the fluorometer with a single optical lens, the optical emitters may direct light into and the detector may receive light from substantially the same portion of fluid adjacent the optical lens. This may help avoid inconsistent optical readings that may otherwise occur if different optical emitters were to emit light through different portions of fluid through physically separate optical lenses. In addition, configuring the fluorometer with a single optical lens may provide a comparatively compact fluorometer design that can be utilized in a number of different applications. For instance, depending on the design, the fluorometer housing may be configured to be inserted into a port of a fluid vessel, a leg of a T-section of pipe, or other mechanical fitting of a process system. This can allow that fluorometer to be readily installed as an on-line fluorometer to optically monitor the process.

While the fluorometer design can vary, in some additional examples, the fluorometer includes one or more supplemental sensors that are configured to measure non-optical characteristics of the fluid sample under analysis. For example, the fluorometer may include a temperature sensor, a pH sensor, an electrical conductivity sensor, a flow rate sensor, a pressure sensor, and/or any other suitable type of sensor. Such supplemental sensors may have sensor interfaces located on the external surface of the fluorometer housing, e.g., adjacent the optical lens of the fluorometer, with sensor electronics positioned inside the housing. The supplemental sensors can measure non-optical properties of substantially the same portion of fluid being optically analyzed by the fluorometer. By measuring both optical and non-optical properties of the fluid under analysis, a process utilizing the fluid may be benchmarked and controlled more accurately than if only optical or non-optical properties of the fluid were measured.

In one example, an optical sensor is described that includes a housing, a first optical emitter, a second optical emitter, and an optical detector. According to the example, the housing defines an optical pathway configured to direct light through a lens optically coupled to the optical pathway into a fluid sample and to receive light from the fluid sample. The first optical emitter is configured to emit light at a first wavelength through the optical pathway into the sample. The second optical emitter is configured to emit light at a second wavelength through the optical pathway into the sample. In addition, the optical detector is configured to receive light from the fluid sample through the optical pathway.

In some embodiments, the first and second wavelengths are such that the first wavelength excites fluorescence in the sample while the second wavelength scatters off the sample. The detector can detect the fluoresced light from the sample in order to determine a characteristic of the sample, such as the concentration of a fluorophore. In some embodiments, the detector also measures the scattered light from the sample in order to determine another property of the sample which may have an effect on the fluorescence thereof, such as the turbidity of the sample. The amount of scattered light detected in these examples can be used to adjust the amount of fluorescent light detected and, correspondingly, any fluid characteristics determined based on the detected fluorescent emissions. For example, a highly turbid fluid sample may generate fewer fluorescent emissions than a less turbid fluid sample, even though the highly turbid fluid sample has a higher concentration of fluorophores. This can occur if the turbidity in the fluid sample blocks fluorescent emissions that would otherwise be detected by the fluorometer. Accordingly, with knowledge of the turbidity of the fluid sample, the fluorescent emission detected from the fluid sample can be adjusted accordingly.

An optical sensor according to the disclosure can have a number of different detector configurations. In one example, the optical sensor includes a single optical detector that receives fluorescent emissions emitted from a fluid sample under analysis and also receives light scattered from the fluid sample under analysis. The optical detector may receive the light through a single optical lens mounted on an external surface of the optical detector housing. In such examples, the optical sensor may alternatingly emit light from the first optical emitter configured to generate fluorescent emissions while the second optical emitter configured to generate scattered light is off and then emit light from the second optical emitter while the first optical emitter is off. In such examples, the single optical detector may alternatingly receive fluorescent emissions emitted from the fluid sample in response to light from the first optical emitter and light scattered from the fluid sample in response to light from the second optical emitter, providing different detection channels for the same optical detector. In other examples, the optical sensor includes multiple optical detectors, including one optical detector configured to measure fluorescent emissions emitted from a fluid sample in response to light from the first optical emitter and a second optical detector configured to measure light scattered from the fluid sample in response to light from the second optical emitter. The first and second optical emitters may emit light into the fluid sample simultaneously in these examples.

In some additional examples, the optical sensor includes a reference detector configured to measure light from the first and second optical emitters prior to their being incident on the sample. In this way, the amount of light incident on the sample to cause scattering and fluorescence can be determined. This information can be used to scale the detected scattered and fluoresced light, as the amount of light scattered and fluoresced is generally a function of the amount of light incident on the sample. Accordingly, when used, the reference detector can act to calibrate the detector and provide a reference point for the measurements made by the first optical detector.

In various embodiments, the optical sensor includes an optical pathway through which light is guided from the optical emitters to the sample and guided back from the sample to the optical detector. Various optical components including partially reflective optical windows and filters can direct light toward its desired destination while preventing unwanted light from interfering with measurements. Additional optical pathways may be provided to guide light to and from these optical components. For example, in some embodiments, the optical sensor includes a partially reflective optical window that functions to direct portions of light from the first and second optical emitters both to the second optical detector (e.g., reference detector) and toward the optical pathway. In these embodiments, another partially reflective optical window may direct portions of the light from each emitter toward the sample via the optical pathway. In some embodiments, light scattered and/or fluoresced from the sample travel back through the optical pathway and are transmitted through the partially reflective optical window toward the first optical detector.

In one example, a system is described that includes an optical sensor and a controller. The optical sensor includes a housing having an optical pathway configured to direct light through a lens optically connected to the optical pathway into a fluid sample under analysis and receive light from the fluid sample through the lens. The optical sensor also includes a first optical emitter, a second optical emitter, and an optical detector. According to the example, the controller is configured to control the first optical emitter to emit light at a first wavelength through the optical pathway into the fluid sample under analysis, detect fluorescent emissions emitted by the fluid sample and received through the optical pathway via the optical detector, control the second optical emitter to emit light at a second wavelength different than the first wavelength through the optical pathway and into the fluid sample under analysis, and detect light scattered by the fluid sample and received through the optical pathway by the optical detector.

In a variety of embodiments, the sensor includes an optical emitter assembly coupled to the optical sensor and at least partially disposed in the optical pathway. The optical emitter assembly can be fixedly or removably coupled to the sensor. In some examples, the optical emitter assembly can include the second optical emitter. In some configurations, the optical emitter assembly is positioned in the optical pathway such that it blocks a portion of light from the first optical emitter from reaching the optical lens to be emitted to the fluid sample. The optical emitter assembly can include a reference optical detector for detecting light emitted by the second optical emitter disposed in the optical emitter assembly.

In another example, a method is described including emitting light at first wavelength by a first optical emitter through an optical pathway into a fluid sample, and receiving fluorescent emissions emitted by the fluid sample through the optical pathway by an optical detector. The method further includes emitting light at a second wavelength different than the first wavelength by a second optical emitter through the optical pathway and into the fluid sample, and receiving light scattered by the fluid sample through the optical pathway by the optical detector. The second optical emitter can be positioned in the optical pathway, for example, in an optical emitter assembly. Various methods include emitting both the first and second wavelengths of light simultaneously, or alternatively, alternatingly. In some embodiments, receiving light fluoresced by the sample is done while emitting light from the first optical emitter, while in alternative embodiments it is done subsequent to ceasing emission from the first optical emitter.

The details of one or more examples are set forth in the accompanying drawings and the description below. Other features, objects, and advantages will be apparent from the description and drawings, and from the claims.

DETAILED DESCRIPTION

Figure 1:
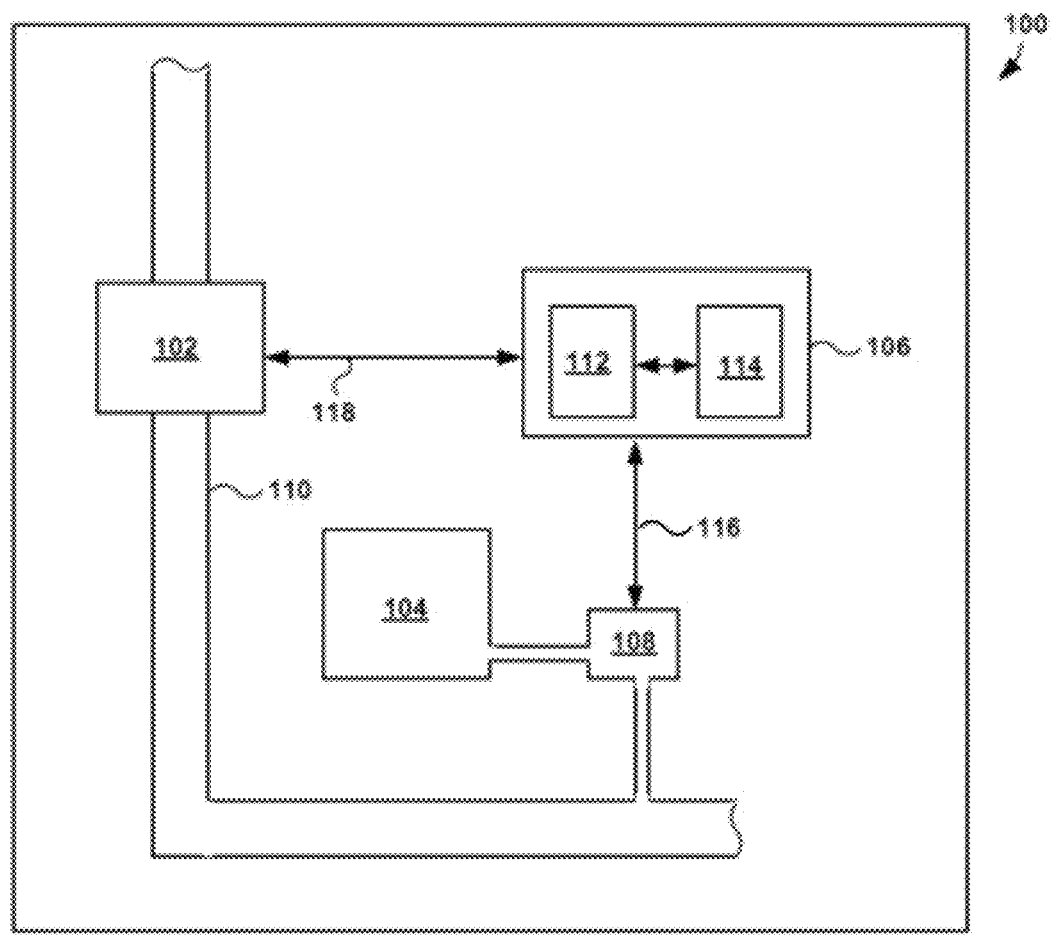
FIG. 1 is a diagram illustrating an example fluid system that may include an optical sensor according to examples of the disclosure.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Optical sensors are used in a variety of applications, including monitoring industrial processes. An optical sensor can be implemented as a portable, hand-held device that is used to periodically analyze the optical characteristics of a fluid in an industrial process. Alternatively, an optical sensor can be installed online to continuously analyze the optical characteristics of a fluid in an industrial process. In either case, the optical sensor may optically analyze the fluid sample and determine different characteristics of the fluid, such as the concentration of one or more chemical species in the fluid.

As one example, optical sensors are often used in industrial cleaning and sanitizing applications. During an industrial cleaning and sanitizing process, water is typically pumped through an industrial piping system to flush the piping system of product residing in pipes and any contamination build-up inside the pipes. The water may also contain a sanitizing agent that functions to sanitize and disinfect the piping system. The cleaning and sanitizing process can prepare the piping system to receive new product and/or a different product than was previously processed on the system.

An optical sensor can be used to monitor the characteristics of flushing and/or sanitizing water flowing through a piping system during an industrial cleaning and sanitizing process. Either continuously or on an intermittent basis, samples of water are extracted from the piping system and delivered to the optical sensor. Within the optical sensor, light is emitted into the water sample and used to evaluate the characteristics of the water sample. The optical sensor may determine whether residual product in the piping system has been sufficiently flushed out of the pipes, for example, by determining that there is little or no residual product in the water sample. The optical sensor may also determine the concentration of sanitizer in the water sample, for example, by measuring a fluorescent signal emitted by the sanitizer in response to the light emitted into the water sample. If it is determined that there is an insufficient amount of sanitizer in the water sample to properly sanitize the piping system, the amount of sanitizer is increased to ensure proper sanitizing of the system.

While the optical sensor can have a variety of different configurations, in some examples, the optical sensor is designed to have a single optical lens through which light is emitted into a fluid sample and also received from the fluid sample. The optical sensor may include a housing that contains various electronic components of the sensor and also has optical pathways to control light movement to and from the single optical lens. Such an arrangement may facilitate design of a compact optical sensor that can be readily installed through a variety of mechanical pipe and process fittings to optically analyze a desired process fluid.

FIG. 1 is a conceptual diagram illustrating an example fluid system 100, which may be used to produce a chemical solution having fluorescent properties, such as a sanitizer solution exhibiting fluorescent properties. Fluid system 100 includes optical sensor 102, a reservoir 104, a controller 106, and a pump 108. Reservoir 104 may store a concentrated chemical agent that can be blended with a diluent, such as water, to generate the chemical solution, or can be any other source for the sample to be characterized. Optical sensor 102 is optically connected to fluid pathway 110 and is configured to determine one or more characteristics of the solution traveling through the fluid pathway.

The fluid pathway 110 can be a single fluid vessel or combination of vessels which carry a fluid sample through the fluid system 100 including, but not limited to, pipes, tanks, valves, pipe tees and junctions, and the like. In some instances, one or more components of the fluid pathway 110 can define an interface or opening sized to receive or otherwise engage with the optical sensor 102. In operation, optical sensor 102 can communicate with controller 106, and controller 106 can control fluid system 100 based on the fluid characteristic information generated by the optical sensor.

Controller 106 is communicatively connected to optical sensor 102 and pump 108. Controller 106 includes processor 112 and memory 114. Controller 106 communicates with pump 108 via a connection 116. Signals generated by optical sensor 102 are communicated to controller 106 via a wired or wireless connection, which in the example of FIG. 1 is illustrated as wired connection 118. Memory 114 stores software for running controller 106 and may also store data generated or received by processor 112, e.g., from optical sensor 102. Processor 112 runs software stored in memory 114 to manage the operation of fluid system 100.

As described in greater detail below, optical sensor 102 is configured to optically analyze a sample of fluid flowing through fluid pathway 110. Optical sensor 102 may include an optical detector that is positioned and configured to measure fluorescent emissions emitted by the fluid sample. In some configurations, a single optical detector can be used to measure both scattering and fluorescence from a sample and can receive both scattered and fluoresced light via a single optical pathway in the sensor 102. The single optical pathway can additionally be used to direct light to induce scattering and fluorescence to the sample, thereby providing a compact and spatially efficient interface between the sensor 102 and the sample. Providing a single optical communication point between the sensor 102 and sample also can simplify implementation of the sensor 102 into fluid system 100, e.g., by providing a sensor that can easily interface with one or more components of the fluid pathway 110 such as a tee configuration in a pipe.

In the example of FIG. 1, fluid system 100 is configured to generate or otherwise receive a chemical solution having fluorescent properties. Fluid system 100 can combine one or more concentrated chemical agents stored within or received from reservoir 104 with water or another diluting fluid to produce the chemical solutions. In some instances, dilution is not necessary, as the reservoir immediately provides an appropriate sample. Example chemical solutions that may be produced by fluid system 100 include, but are not limited to, cleaning agents, sanitizing agents, cooling water for industrial cooling towers, biocides such as pesticides, anti-corrosion agents, anti-scaling agents, anti-fouling agents, laundry detergents, clean-in-place (CIP) cleaners, floor coatings, vehicle care compositions, water care compositions, bottle washing compositions, and the like.

The chemical solutions generated by or flowing through the fluid system 100 may emit fluorescent radiation in response to optical energy directed into the solutions by optical sensor 102. Optical sensor 102 can then detect the emitted fluorescent radiation and determine various characteristics of the solution, such as a concentration of one or more chemical compounds in the solution, based on the magnitude of the emitted fluorescent radiation. In some embodiments, the optical sensor 102 can direct optical energy to the solution and receive fluorescent radiation from the solution via an optical pathway within the optical sensor 102, allowing for a compact design for the optical sensor 102.

In order to enable optical sensor 102 to detect fluorescent emissions, the fluid generated by fluid system 100 and received by optical sensor 102 may include a molecule that exhibits fluorescent characteristics. In some examples, the fluid includes a polycyclic compound and/or a benzene molecule that has one or more substituent electron donating groups such as, e.g., —OH, —$NH_2$, and —$OCH_3$, which may exhibit fluorescent characteristics. Depending on the application, these compounds may be naturally present in the chemical solutions generated by fluid system 100 because of the functional properties (e.g., cleaning and sanitizing properties) imparted to the solutions by the compounds.

In addition to or in lieu of a naturally fluorescing compound, the fluid generated by fluid system 100 and received by optical sensor 102 may include a fluorescent tracer (which may also be referred to as a fluorescent marker). The fluorescent tracer can be incorporated into the fluid specifically to impart fluorescing properties to the fluid. Example fluorescent tracer compounds include, but are not limited to, naphthalene disulfonate (NDSA), 2-naphthalenesulfonic acid, Acid Yellow 7,1,3,6,8-pyrenetetrasulfonic acid sodium salt, and fluorescein.

Independent of the specific composition of the fluid generated by fluid system 100, the system can generate fluid in any suitable fashion. Under the control of controller 106, pump 108 can mechanically pump a defined quantity of concentrated chemical agent out of reservoir 104 and combine the chemical agent with water to generate a liquid solution suitable for the intended application. Fluid pathway 110 can then convey the liquid solution to an intended discharge location. In some examples, fluid system 100 may generate a flow of liquid solution continuously for a period of time such as, e.g., a period of greater than 5 minutes, a period of greater than 30 minutes, or even a period of greater than 24 hours. Fluid system 100 may generate solution continuously in that the flow of solution passing through fluid pathway 110 may be substantially or entirely uninterrupted over the period of time.

In some examples, monitoring the characteristics of the fluid flowing through fluid pathway 110 can help ensure that the fluid is appropriately formulated for an intended downstream application. Monitoring the characteristics of the fluid flowing through fluid pathway 110 can also provide feedback information, e.g., for adjusting parameters used to generate new fluid solution. For these and other reasons, fluid system 100 can include a sensor to determine various characteristics of the fluid generated by the system. The sensor can engage directly with the fluid pathway 110 to monitor fluid characteristics, or can alternatively receive fluid from the fluid system 100 separately from the fluid pathway 110.

In the example of FIG. 1, fluid system 100 includes optical sensor 102. The optical sensor 102 can engage the fluid pathway 110 in any number of ways, such as interfacing with a tee configuration in a pipe in the fluid pathway 110, being inserted into a port of a tank or other fluid vessel through which fluid periodically flows, or the like. Optical sensor 102 may determine one or more characteristics of the fluid flowing through fluid pathway 110. Example characteristics include, but are not limited to, the concentration of one or more chemical compounds within the fluid (e.g., the concentration of one or more active agents added from reservoir 104 and/or the concentration of one or more materials being flushed from piping in fluid system 100), the temperature of the fluid, the conductivity of the fluid, the pH of the fluid, the flow rate at which the fluid moves through the optical sensor, and/or other characteristics of the fluid that may help ensure the system from which the fluid sample being analyzed is operating properly. Optical sensor 102 may communicate detected characteristic information to controller 106 via connection 118.

Optical sensor 102 may be controlled by controller 106 or one or more other controllers within fluid system 100. For example, optical sensor 102 may include a device controller (not illustrated in FIG. 1) that controls the optical sensor to emit light into the fluid under analysis and also to detect light received back from the fluid. The device controller may be positioned physically adjacent to the other components of the optical sensor, such as inside a housing that houses a light source and detector of the optical sensor. In such examples, controller 106 may function as a system controller that is communicatively coupled to the device controller of optical sensor 102. The system controller 106 may control fluid system 100 based on optical characteristic data received from and/or generated by the device controller. In other examples, optical sensor 102 does not include a separate device controller but instead is controlled by controller 106 that also controls fluid system 100. Therefore, although optical sensor 102 is generally described as being controlled by controller 106, it should be appreciated that fluid system 100 may include one or more controllers (e.g., two, three, or more), working alone or in combination, to perform the functions attributed to optical sensor 102 and controller 106 in this disclosure. Devices described as controllers may include processors, such as microprocessors, digital signal processors (DSPs), application specific integrated circuits (ASICs), field programmable gate arrays (FPGAs), or any other equivalent integrated or discrete logic circuitry, as well as any combinations of such components.

In the example illustrated in FIG. 1, processor 112 of controller 106 can receive determined optical characteristic information from optical sensor 102 and compare the determined characteristic information to one or more thresholds stored in memory 114, such as one or more concentration thresholds. Based on the comparison, controller 106 may adjust fluid system 100, e.g., so that the detected characteristic matches a target value for the characteristic. In some examples, controller 106 starts and/or stops pump 108 or increases and/or decreases the rate of pump 108 to adjust the concentration of a chemical compound flowing through fluid pathway 110. Starting pump 108 or increasing the operating rate of pump 108 can increase the concentration of the chemical compound in the fluid. Stopping pump 108 or decreasing the operating rate of pump 108 can decrease the concentration of chemical compound in the fluid. In some additional examples, controller 106 may control the flow of water that mixes with a chemical compound in reservoir 104 based on determined characteristic information, for example, by starting or stopping a pump that controls the flow of water or by increasing or decreasing the rate at which the pump operates. Although not illustrated in the example fluid system 100 of FIG. 1, controller 106 may also be communicatively coupled to a heat exchanger, heater, and/or cooler to adjust the temperature of fluid flowing through fluid pathway 110 based on characteristic information received from optical sensor 102.

In yet other examples, optical sensor 102 may be used to determine one or more characteristics of a stationary volume of fluid that does not flow through a flow chamber of the optical sensor. For example, optical sensor 102 may be implemented as an offline monitoring tool (e.g., as a handheld sensor), that requires filling the optical sensor with a fluid sample manually extracted from fluid system 100. Alternatively, the optical sensor 102 can engage a portion of the fluid system 100 configured to receive and hold a stationary volume of the fluid, such as a stop-flow device, or an otherwise external vessel for receiving fluid and engaging the optical sensor 102. In some embodiments, a controller 106 can control a system of pumps and/or valves to direct a finite amount of the sample to be measured into such a stationary vessel outfitted with a sensor 102.

Fluid system 100 in the example of FIG. 1 also includes reservoir 104, pump 108, and fluid pathway 110. Reservoir 104 may be any type of container that stores a chemical agent for subsequent delivery including, e.g., a tank, a tote, a bottle, and a box. Reservoir 104 may store a liquid, a solid (e.g., powder), and/or a gas. Pump 108 may be any form of pumping mechanism that supplies fluid from reservoir 104. For example, pump 108 may comprise a peristaltic pump or other form of continuous pump, a positive-displacement pump, or any other type of pump appropriate for the particular application. In examples in which reservoir 104 stores a solid and/or a gas, pump 108 may be replaced with a different type of metering device configured to deliver the gas and/or solid chemical agent to an intended discharge location. Fluid pathway 110 in fluid system 100 may be any type of flexible or inflexible tubing, piping, or conduit.

Figure 2:
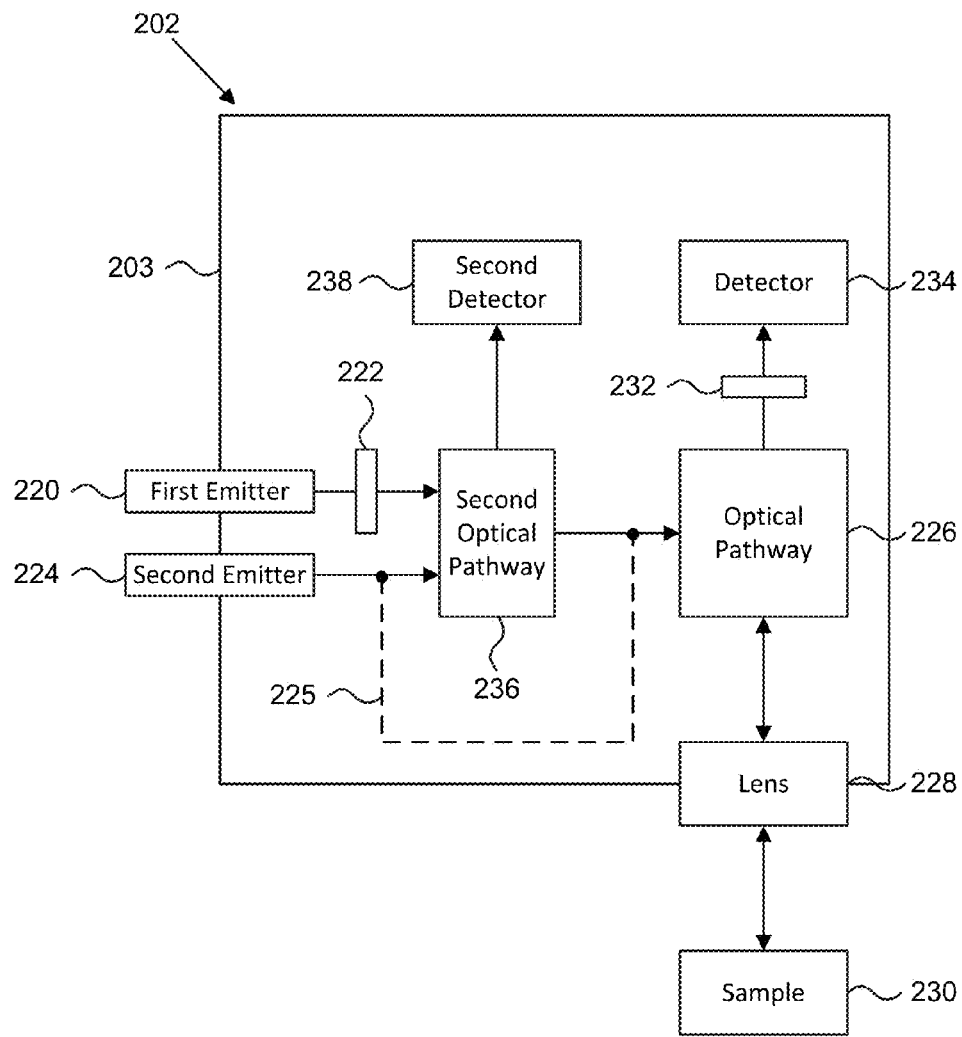
FIG. 2 is a block diagram of an example optical sensor that can determine at least one characteristic of a fluid sample.

In the example of FIG. 1, optical sensor 102 determines a characteristic of the fluid flowing through fluid pathway 110 (e.g., concentration of a chemical compound, temperature or the like) and controller 106 controls fluid system 100 based on the determined characteristic and, e.g., a target characteristic stored in memory 114. FIG. 2 is a block diagram of an example optical sensor 202 that can be installed in fluid system 100 to monitor a characteristic of a fluid flowing through fluid pathway 110. Sensor 202 may be used as optical sensor 102 in fluid system 100, or sensor 202 may be used in other applications beyond fluid system 100.

In the example of FIG. 2, the sensor 202 includes a housing 203, a first optical emitter 220, a second optical emitter 224, an optical window 228, and an optical detector 234. The housing 203 houses the first optical emitter 220, the second optical emitter 224, and the optical detector 234. Optical window 228 is positioned on an external surface of the housing 203 to provide a fluid-tight, optically transmissive barrier between an interior of the housing and fluid in fluid sample 230 that contacts the external surface of the housing. In operation, first optical emitter 220 and second optical emitter 224 emit light that is directed through optical window 228 and into the fluid sample 230 under analysis. In response to light emitted by the first optical emitter 220 and/or the second optical emitter 224 impinging on the fluid adjacent optical window 228, the fluid may scatter light and/or generate fluorescent emissions. The scattered light and/or fluorescent emissions can pass through optical window 228 to be detected by optical detector 234.

To control light transmission to and from optical window 228, optical sensor 202 includes at least one optical pathway 226 optically connecting various components of the optical sensor to the fluid sample 230 under analysis. The optical pathway 226 may guide light emitted by the first optical emitter 220 and second optical emitter 224 so the light is guided from the optical emitters, through optical lens 228, and into fluid sample 230. The optical pathway 226 may also guide light received from the fluid sample 230 through optical window 228 so the light is guided to the optical detector 234. When so configured, the first optical emitter 220 and the second optical emitter 224 may be positioned inside of the housing 203 to direct light into the optical pathway 226 and the optical detector 234 may be positioned inside of the housing to receive light from the optical pathway. Such an arrangement may allow optical sensor 202 to be configured with a single optical lens through which multiple light sources emit light and through which light is also received and detected from a fluid sample under analysis. This may help minimize the size of optical sensor 202, for example, so that the sensor is sufficiently compact to be inserted through a mechanical pipe fitting into a piece of process equipment containing fluid for analysis.

Optical sensor 202 can include any suitable number of optical pathways optically connecting various emitter and detector components housed inside the housing 203 to the fluid sample under analysis via optical window 228. In the example of FIG. 2, optical sensor 202 is conceptually illustrated as having a first optical pathway 226 and a second optical pathway 236. The second optical pathway 236 is optically connected to the first optical pathway 226 and also optically connected to the first optical emitter 220 and the second optical emitter 224. The second optical pathway 236 can receive light from the first optical emitter 220 and second optical emitter 224 and guide the light to the first optical pathway 226 which, in turn, guides the light through optical window 228 into the fluid sample 230 under analysis. In some alternative embodiments, one optical emitter can emit light into the second optical pathway 236 while a second optical emitter is configured to emit light directly into the first optical pathway 226. For example, in some embodiments, the first optical emitter 220 is configured to emit light into the second optical pathway 236 while the second optical emitter 224 is configured to emit light directly to the first optical pathway 226 by way of optical connection 225. It should be noted that the diagram of FIG. 2 is intended to show optical connection and does not necessarily illustrate literal optical paths. For example, in some embodiments, the second optical emitter 224 is positioned proximate the first optical pathway 226, and optical connection 225 need not be a literal bypass of the second optical pathways 236. Rather, optical connection 225 merely illustrates that the second optical emitter 224 may be optically coupled directly to the first optical pathway 226 while the first optical emitter 220 is optically coupled to the first optical pathway 226 by way of the second optical pathway 236. By configuring optical sensor 202 with additional optical pathways, various light emitters and detectors in the optical sensor can be optically connected to the fluid sample under analysis without being positioned directly adjacent the first optical pathway 226.

Optical pathways in optical sensor 202 may be channels, segments of optically conductive tubing (e.g., fiber optic lines), or ducts that allow light to be conveyed through the optical sensor. The optical pathways may also be machined or cast into the housing 203 of the optical sensor. In different examples, the optical pathways may or may not be surrounded by optically opaque material, e.g., to bound light movement through the optical pathways and to prevent light from escaping through the sides of the optical pathways. When optical sensor 202 includes multiple optical pathways, the intersection of one optical pathway with another optical pathway may be defined where light traveling linearly through the one optical pathway is required to change direction to travel through the other optical pathway.

In the example of FIG. 2, the optical sensor 202 includes at least one light source, and, in the illustrated example, is shown with two light sources: first optical emitter 220 and second optical emitter 224. Each of the first optical emitter 220 and the second optical emitter 224 is a light source and can be implemented using any appropriate light source, such as a laser, a lamp, an LED, or the like. In some embodiments, the first optical emitter 220 and/or the second optical emitter 224 are configured to emit substantially uncollimated beams of light into the optical pathway 226. In this case, the optical sensor 202 can include optical components to collimate the light from the first optical emitter 220 and/or the second optical emitter 224 in order to achieve a higher optical efficiency during operation.

Configuring the optical sensor 202 with multiple light sources may be useful, for example, to emit light at different wavelengths into the fluid sample 230. For example, the first optical emitter 220 may be configured to emit light within a first range of wavelengths into the fluid sample 230 to generate fluorescent emissions within the fluid. The second optical emitter 224 may be configured to emit light within a second range of wavelengths different than the first range of wavelengths to measure the amount of light scattered by fluid sample 230.

Independent of the specific number of light sources included in optical sensor 202, the optical sensor includes an optical window 228 through which light is directed into and received from the fluid sample 230. In some examples, optical window 228 focuses light directed into and/or received from the fluid sample under analysis. In such examples, optical window 228 may be referred to as an optical lens. In other examples, optical window 228 passes light directed into and/or received from the fluid sample without focusing the light. Therefore, although optical window 228 is also referred to as optical lens 228 in this disclosure, it should be appreciated that an optical sensor in accordance with the disclosure can have an optical window that does or does not focus light.

Optical window 228 is optically connected to optical pathways 226 and, in some examples, physically connected at a terminal end of the optical pathway. In different examples, the optical window 228 is formed of a single lens or a system of lenses able to direct light into and receive light from the fluid sample 230. The optical window 228 can be integral (permanently attached) to the housing 203 or can be removable from the housing. In some examples, optical window 228 is an optical lens formed by a ball lens positioned within optical pathway 226 to seal the optical pathway and prevent fluid from fluid sample 230 from entering the optical pathway. In such examples, the ball lens may extend distally from an external face of the housing 203, e.g., into a moving flow of fluid. The optical lens 228 can be fabricated from glass, sapphire, or other suitable optically transparent materials.

As briefly mentioned above, the optical pathway 226 is configured to direct light through an optical window 228 optically connected to the optical pathway and also to receive light from the fluid sample through the optical window 228. To detect the light received from the fluid sample under analysis, optical sensor 202 includes at least one optical detector 234 optically connected to optical pathway 226. The optical detector 234 can be implemented using any appropriate detector for detecting light, such as a solid-state photodiode or photomultiplier, for example. The optical detector 234 may be sensitive to, and therefore detect, only a narrow band of wavelengths. Alternatively, the optical detector 234 may be sensitive to, and therefore detect, a wide range of light wavelengths.

During operation, light is emitted into the fluid sample 230 via the optical window 228 optically connected to the optical pathway 226. The window 228 can additionally collect light from the fluid sample 230, such as light scattered off of the sample or emitted by the sample via a mechanism such as fluorescence. Such light can be directed from the fluid sample 230 back into the optical pathway 226 via the window 228 and received by optical detector 234.

To control the wavelengths of light emitted by the optical emitters and/or detected by the optical detector in sensor 202, the optical sensor may include an optical filter. The optical filter can filter wavelengths of light emitted by the optical emitters and/or received by optical detectors, e.g., so that only certain wavelengths of light are emitted into fluid sample 230 and/or received from the fluid sample and detected by optical detector 234.

For example, the sensor 202 may include an optical filter 232 configured to prevent unwanted light received from fluid sample 230 from impinging on the optical detector 234. If the detection of a particular wavelength or band of wavelengths is desired but the optical detector 234 is sensitive to a wider band or otherwise large number of wavelengths, the filter 232 can act to prevent light outside of the desired band from impinging on the optical detector 234. The filter 232 can absorb or reflect light that it does not allow to pass through.

According to some embodiments, one of the first optical emitter 220 and second optical emitter 224 may emit a wider band of wavelengths than is desired or useful for use with the sensor 202, as will be explained in more detail below. Accordingly, sensor 202 can include a filter 222 disposed between the first 220 and/or the second 224 optical emitter and the fluid sample 230. The filter 222 may be configured to prevent certain wavelengths of light from reaching the fluid sample 230 via the optical pathway 226. Such a filter 222 can be positioned to at least partially filter light from either one or both of the first optical emitter 220 and the second optical emitter 224. For example, in FIG. 2, the optical filter 222 is shown disposed between the first optical emitter 220 and the second optical pathway 236.

During operation, the optical sensor 202 can control the first optical emitter 220 to emit light at a first wavelength (e.g., range of wavelengths) into the fluid sample 230, control the second optical emitter 224 to emit light at a second wavelength (e.g., range of wavelengths) into the fluid sample, and receive light from the fluid sample at optical detector 234. According to some embodiments, the first optical emitter 220 is configured to emit light at a wavelength sufficient to cause molecules in the fluid sample 230 under analysis to fluoresce. Light fluoresced by the fluid sample 230 may be collected by the optical window 228 and directed into the optical pathway 226 as an emission beam. Additionally, the second optical emitter 224 may be configured to emit light at a wavelength sufficient to cause light scattering by the fluid sample 230 under analysis. Such light scattering may occur when the fluid sample 230 is turbid, e.g., and contains light reflective particles. Light scattered by the fluid sample 230 may be collected by optical window 228 and directed back into the optical pathway 226 as a scattering beam.

Although the wavelengths can vary, in some examples, the first optical emitter 220 is configured to emit light within a wavelength ranging from approximately 225 nanometers (nm) to approximately 700 nm, such as from approximately 250 nm to approximately 350 nm, or from approximately 265 nm to approximately 290 nm. The second optical emitter 224 may emit light at a wavelength ranging from approximately 750 nm to approximately 1200 nm, such as from approximately 800 nm to approximately 900 nm. For example, the first optical emitter 220 may emit light within the ultraviolet (UV) spectrum while the second optical emitter 224 emits light within the infrared (IR) spectrum. Other wavelengths are both contemplated and possible, and it should be appreciated that the disclosure is not limited in this respect.

To detect light emanating from the fluid sample 230 under analysis (e.g., fluorescent emissions, light scattering), the sensor 202 of FIG. 2 further includes an optical detector 234. Optical detector 234 is optically connected to optical pathway 226 and may receive at least a portion of the fluorescent emission beam and the scattered light beam transmitted through the optical window 228 from the fluid sample 230 under analysis. Upon entering housing 203, the received portions of the fluorescent emission beam and scattered light beam may be directed to the optical detector via the optical pathway 226 for measurement and/or analysis. In some embodiments, the intensities of the beams are measured by the optical detector 234 and used to determine information about the sample, such as the concentration of a particular component (e.g., a fluorescing compound and/or a non-fluorescing compound) contained therein. Information about the fluid sample under analysis carried by scattered light and fluorescent emissions received from the fluid sample and detected by optical detector 234 may provide different channels of information, e.g., for characterizing the fluid sample and/or controlling the system containing the fluid sample.

For example, the optical sensor 202 may use light scattering information detected by optical detector 234 to adjust or correct the amount of fluorescent emissions detected by the optical sensor and/or calculations based on the measured fluorescent emissions. The turbidity of the fluid sample under analysis may affect the magnitude of the fluorescent emissions generated by the fluid sample and/or received by optical detector 234. Optical sensor 202 may compensate for these turbidity effects by measuring the amount of turbidity in the fluid sample, which may be proportional to the amount of light scattered by the fluid sample, and adjusting the magnitude of the measured fluorescent emissions based on the turbidity measurement. In another configuration, the optical sensor 202 can adjust the calculation based on the measured fluorescence (e.g., concentration) to incorporate the measured turbidity. In addition, optical detector 234 may measure the amount of light scattered by the fluid sample 230 in response to light emitted by the second optical emitter 224 and determine other characteristics of the fluid sample. For example, the optical sensor 202 may determine a concentration of a non-fluorescing species (e.g., a contaminant) in the fluid sample based on the amount of light scattered by the fluid sample and, e.g., calibration data stored in memory. For instance, if the fluid sample 230 under analysis has a first concentration of a non-fluorescing chemical compound(s), the optical detector 234 may detect a first magnitude of scattered light. However, if the fluid sample has a second concentration of the non-fluorescing chemical compound(s) that is greater than the first concentration, the optical detector 234 may detect a second magnitude of scattered light that is greater than the first magnitude.

Optical sensor 202 includes at least one, and optionally multiple, optical detectors to detect light received from the fluid sample 230 in response to light emitted by the first optical emitter 220 and/or the second optical emitter 224. To measure the amount of light emitted by the first optical emitter 220 and/or the second optical emitter 224 into the fluid sample 230 under analysis, optical sensor 202 may also include at least one reference optical detector. The reference optical detector may be positioned inside of the housing 203 and configured to measure light emitted by the first optical emitter 220 and/or the second optical emitter 224. The amount of light received from the fluid sample 230 in response to light emitted by the first optical emitter 220 and/or the second optical emitter 224 may vary based on the amount of light originally emitted by the first and second optical emitters. Accordingly, light measurements made by the reference optical detector can be used to adjust light measurements made by optical detector 234.

In the embodiment of FIG. 2, optical sensor 202 includes a second optical detector 238 that can function as a reference optical detector. Second optical detector 238 is in optical communication with the second optical pathway 236 and is configured to receive light therefrom. In some embodiments, the second optical detector 238 is configured to receive light from both the first optical emitter 220 and the second optical emitter 224, e.g., in alternating sequence. Such light can be measured at the second optical detector 238 in order to determine operating conditions of the sensor, calibrate the sensor, or to perform any other useful function associated with the sensor. In an exemplary embodiment, the second optical detector 238 can detect light received from the first optical emitter 220 and then detect light received from the second optical emitter 224. Optical sensor 202 may then determine the relative intensities or an intensity ratio between light emitted from the two optical emitters. This information can be used to supplement the information determined about the fluid sample under analysis, such as adjusting a fluid characteristic determined based on light received by the first optical detector 234.

Optical sensor 202 is configured to measure at least one optical characteristic of the fluid sample 230 under analysis. To supplement optical characteristic information generated by the optical sensor 202, the sensor may include one or more non-optical sensors configured to measure non-optical characteristics of the fluid sample 230 under analysis. The non-optical sensor hardware/software may be housed within housing 203 and include a contact extending through an external surface of the housing (e.g., adjacent to optical lens 228) for measuring a non-optical property of the fluid sample under analysis. As examples, optical sensor 202 may include a temperature sensor, a pH sensor, an electrical conductivity sensor, and/or a flow rate sensor. When used, the temperature sensor may sense a temperature of the fluid adjacent the sensor; the pH sensor may determine a pH of the fluid adjacent the sensor; the conductivity sensor may determine an electrical conductivity of the fluid adjacent the sensor; and the flow sensor may monitor a rate of fluid flowing past the sensor. In one example, optical sensor 202 includes both a temperature sensor and an electrical conductivity sensor. Optical sensor 202 may include additional or different non-optical sensors, and the disclosure is not limited to an optical sensor that utilizes any particular type of non-optical sensor.

Figure 3:
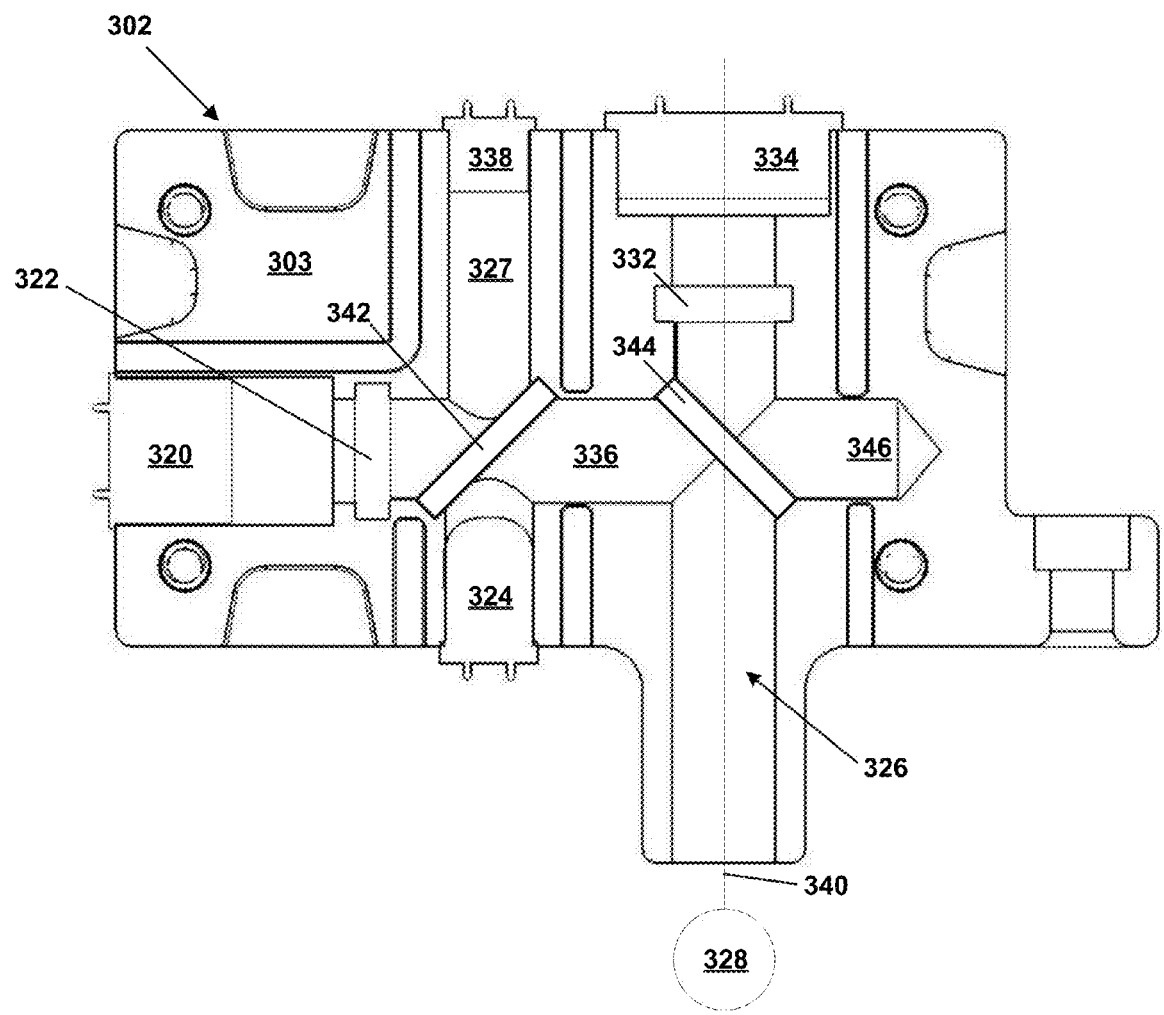
FIG. 3 is a schematic drawing of an example arrangement of components that may be used for the optical sensor of FIG. 2.

The sensor 202 of FIG. 2 can have a number of different physical configurations. Some such examples are described in patent application Ser. No. 14/039,683, which was filed on Sep. 27, 2013, and is hereby incorporated by reference in its entirety. FIG. 3 is a schematic drawing of an example arrangement of components that may be used for the optical sensor of FIG. 2. FIG. 3 shows a sensor 302 for measuring at least one property of a fluid sample. Similar to the sensor of FIG. 2, sensor 302 comprises a first optical emitter 320 and a second optical emitter 324. First 320 and second 324 optical emitters can include any appropriate light sources, including those discussed above with respect to FIG. 2. During operation, the first optical emitter 320 can emit light at a first wavelength while the second optical emitter 324 can emit light at a second wavelength. The first wavelength may be the same wavelength or range of wavelengths as the second wavelength, or the first wavelength may be a different wavelength or range of wavelengths as the second wavelength. Depending on the application, the first optical emitter 320 and second optical emitter 324 can emit light within the ultraviolet (UV), infrared (IR), and/or visible light spectrum. In some examples as described above, the first wavelength may cause molecules in the fluid sample under analysis (e.g., fluid sample 230) to excite and fluoresce, while the second wavelength may scatter off the fluid sample under analysis.

Additionally, the first 320 and/or second 324 optical emitter may be such that one or both emit unnecessary or unwanted light in addition to the first or second wavelengths of light desired to be emitted. To prevent such light from undesirably affecting measurements, sensor 302 may include a first optical filter 322 configured to limit the light emitted by the first optical emitter 320 into the sample under analysis. The embodiment of FIG. 3 shows a first optical filter 322 positioned between the first optical emitter 320 and a partially reflective optical window 342. The first optical filter 322 can be configured to filter out, for example, substantially all wavelengths of light within a range of fluorescent light emitted by the fluid sample, when the fluid sample emits fluorescence. Such a filter 322 can help eliminate false fluorescence detection by detector 334 in the sensor due to scattering of light within the same wavelength range as the fluorescent emissions. For example, if the first optical emitter 320 were to emit light within the wavelength of the fluorescent emissions generated by the fluid sample under analysis, the optical detector 334 may detect both fluorescent emissions generated by the fluid sample and light emitted by the first optical emitter 320 and scattered back to the optical detector 334. Optical filter 322 can filter out light emitted by the first optical detector 334 within the wavelength range of the fluorescent emissions.

The sensor 302 in the example of FIG. 3 also includes a housing 303 that houses various hardware/software components of the sensor and controls light movement through the sensor. In some embodiments, the housing 303 contains all or some of the first optical emitter 320 and/or the second optical emitter 324, while in other embodiments, the emitters are located external to the housing 303.

As was the case with the schematic sensor shown in FIG. 2, the embodiment shown in FIG. 3 includes an optical detector 334, an optical window 328 (e.g., optical lens 328) for directing light into and receiving light from a fluid sample, and an optical pathway 326. In the illustrated example, optical lens 328 is shown physically separate from but optically connected to optical pathway 326. In other examples, lens 328 is physically connected (e.g., attached) at a terminal end of the optical pathway.

To control light movement through optical sensor 302, the optical sensor includes at least one optical pathway which, in the illustrated example is shown as three optical pathways: a first optical pathway 326, a second optical pathway 336, and a third optical pathway 327. The optical pathways may define bounded channels, tubes, conduits, or cavities that control light movement through the sensor. The emitters and detectors of optical sensor 302 may be arranged around the optical pathways to direct light into the optical pathways and/or receive light from the optical pathways. For example, the first optical emitter 320 and second optical emitter 324 in FIG. 3 are configured to direct light into the first optical pathway 326 that is optically connected to the optical lens 328 and, subsequently, the fluid sample under analysis. Further, the optical detector 334 in FIG. 3 is configured to receive light from the first optical pathway 326 that propagates from the fluid sample under analysis and travels through optical lens 328.

The optical sensor 302 can have a number of different optical pathway configurations and the configurations can vary, e.g., based on the number of optical emitters and detectors contained in the sensor. In the example of FIG. 3, optical sensor 302 includes the first optical pathway 326 positioned between optical lens 328 and the first optical detector 334. Light traveling linearly through the optical lens 328 (e.g., an optical center of the lens) can travel through the first optical pathway 326 and impinge on the first optical detector 334 (e.g., an optical center of the detector). In such an example, the first optical pathway 326 may define a major axis 340 extending along the length of the pathway and extending through a center of the optical lens 328 (e.g., an optical center) and a center of the first optical detector 334 (e.g., an optical center of the detector). The first optical pathway 326 may be optically connected to a single optical window of the detector (e.g., optical lens 328) to other components housed within housing 303.

The first optical emitter 320 and the second optical emitter 324 are configured to emit light into the first optical pathway 326 and, subsequently, into the fluid sample under analysis. In some examples, the first optical emitter 320 and/or the second optical emitter 324 emit light directly into the first optical pathway 326, e.g., without emitting into an intervening optical pathway that intersects the first optical pathway. In other examples, the first optical emitter 320 and/or the second optical emitter 324 emit light into an intermediate optical pathway that is optically connected to the first optical pathway 326. That is, the first optical emitter 320 and/or the second optical emitter 324 may indirectly emit light into the first optical pathway 326.

In optical sensor 302 in FIG. 3, the first optical emitter 320 is positioned to emit light into the second optical pathway 336 that extends to the first optical pathway 326. Further, in the illustrated embodiment, the second optical emitter 324 is positioned to emit light into the third optical pathway 327 that extends to the second optical pathway 336 which, in turn, extends to the first optical pathway 326. The second optical pathway 336 intersects the first optical pathway 326, allowing at least a portion of the light transmitting from the first optical emitter 320 and second optical emitter 324 to travel through the second optical pathway, into the first optical pathway, and through the optical lens 328. The third optical pathway 327 intersects the second optical pathway, allowing at least a portion of the light transmitting from the second optical emitter 324 to travel through the third optical pathway, into the second optical pathway, into the first optical pathway, and through the optical lens 328.

Although the configuration can vary, the second optical pathway 336 in FIG. 3 intersects the first optical pathway 326 at an approximately 90 degree angle. Further, the third optical pathway 327 intersects the second optical pathway 336 at an approximately 90 degree angle. In some examples, the third optical pathway 327 extends parallel to the first optical pathway 326, while in other examples, the third optical pathway does not extend parallel to the first optical pathway. By arranging the optical emitters and optical detectors of optical sensor 302 around intersecting optical pathways optically connected to a single optical lens 328, the sensor can provide a compact design that is easily installed in a variety of chemical and fluid processes.

In examples in which the optical sensor 302 includes intersecting optical pathways to control light movement, the optical sensor may also include optical elements (e.g., reflectors, partially reflective optical windows) that direct light received from one intersecting optical pathway into another intersecting optical pathway. The optical elements can help control the direction of light movement to optical lens 328 and/or to optical detectors.

In the illustrated example of FIG. 3, the sensor includes a partially reflective optical window 344 that is positioned at the intersection of the first 326 and second 336 optical pathways. The partially reflective optical window 344 is configured to reflect at least a portion of light emitted by the first optical emitter 320 and the second optical emitter 324 from the second optical pathway 336 to the first optical pathway 326. In some embodiments, the partially reflective optical window 344 is further configured to transmit light from the fluid sample and lens 328 to the optical detector 334. Accordingly, the partially reflective optical window can be configured to both transmit and reflect portions of incident light. The angle of the partially reflective optical window 344 relative to the direction of light travel through the first optical pathway may vary, e.g., based on the angle at which the first optical pathway 326 intersects the second optical pathway 336. However, in FIG. 3 where the first optical pathway 326 intersects the second optical pathway 336 at an approximately 90 degree angle, the partially reflective optical window 344 is oriented at approximately a 45 degree angle, e.g., relative to the direction of light travel through both the first optical pathway 326 and the second optical pathway 336.

According to various embodiments, the partially reflective optical window 344 can be configured to reflect or transmit between 0% and 100% of incident light, with the reflection and transmission percentages being wavelength dependent. Any suitable optical element can be used as partially reflective optical window 344. Such a partially reflective optical window 344 can comprise, for example, a dichroic filter, or any other suitable optical component.

In operation, the partially reflective optical window 344 of FIG. 3 is configured to reflect light from the first 320 and second 324 optical emitters from the second optical pathway 336 into the first optical pathway 326 (e.g., approximately 90 degrees). This can change the direction of light emitted by the first optical emitter 320 and the second optical emitter 324 from traveling along the length of the second optical pathway 336 to traveling along the length of first optical pathway 326. While the partially reflective optical window 344 may reflect at least part of the light emitted by the first optical emitter 320 and the second optical emitter 324, e.g., into the fluid sample under analysis, the partially reflective optical window may also allow at least a portion of the light received from the fluid sample to pass through the partially reflective optical window. For example, light scattered by the fluid sample under analysis and/or fluorescent emissions generated by the fluid sample may enter into the first optical pathway 326 and at least partially transmit through the partially reflective optical window 344 (e.g., without being reflected or absorbed by the optical window) to be detected by optical detector 334. In this way, the partially reflective optical window 344 can reflect light received from the optical emitters into the fluid sample and transmit light received from the fluid sample to be detected by the optical detector 334.

In some embodiments, the sensor 302 further includes a beam dump 346, positioned opposite the partially reflective optical window 344 from the first 320 optical emitter along the second optical pathway 336. The beam dump 346 is configured to absorb or trap any light that is incident thereon. For example, in some embodiments, any light that is transmitted from the second optical pathway 336 through the partially reflective optical window 344 will be transmitted to the beam dump 346 where it will be absorbed and prevented from being detected by optical detector 334.

Optical sensor 302 in FIG. 3 also includes a first reference optical detector 338, which may function as a reference optical detector for first 320 and or second 324 optical emitters 320, for example. In the illustrated embodiment, the first reference optical detector 338 is positioned to receive light emitted by at least one of the first optical emitter 320 and the second optical emitter 324. Although the location can vary, in the illustrated example, the second optical detector 338 is positioned on an opposite side of the second optical pathway 336 from the second optical emitter 324. In particular, the second optical detector 338 is positioned at a terminal end of the third optical pathway 327, opposite the second optical emitter 324. In the exemplary embodiment illustrated in FIG. 3, the first optical emitter 320 and second optical emitter 324 are oriented substantially perpendicular to one another, with the first optical emitter 320 being approximately coaxial with the second optical pathway 336 and the second optical emitter 324 being approximately coaxial with a third optical pathway 327. In other examples, the second optical emitter 324 can be positioned at other locations within optical sensor 302, and it should be appreciated that the disclosure is not limited to the specific configuration of FIG. 3. As one example, the position of the first optical emitter 320 and the second optical emitter 324 may be switched so that the first optical emitter is in the position occupied by the second optical emitter shown on FIG. 3 and the second optical emitter is in the position occupied by the first optical emitter.

In examples in which optical sensor 302 includes the third optical pathway 327 intersecting the second optical pathway 336, the sensor may include a partially reflective optical window 342 that is positioned at the intersection of the second 336 and third 327 optical pathways. The partially reflective optical window 342 may be configured to reflect at least a portion of light emitted by the second optical emitter 324 from the third optical pathway into the second optical pathway 336 and also transmit at least a portion of light emitted by the second optical emitter 324 to be received by the second optical detector 338. In addition, the partially reflective optical window 342 may be configured to reflect at least a portion of light emitted by the first optical emitter 320 from the second optical pathway into the third optical pathway 327 to be received by the first reference optical detector 338 and also transmit at least a portion of light emitted by the first optical emitter 320 to pass through the second optical pathway 336 into the first optical pathway 326. Any suitable optical element can be used as partially reflective optical window 342. Such a partially reflective optical window 342 can comprise, for example, a dichroic filter, a quartz window, and/or a sapphire window. In some embodiments, the partially reflective optical window 342 includes an anti-reflective coating.

The angle of the partially reflective optical window 342 relative to the direction of light travel through the second optical pathway 336 may vary, e.g., based on the angle at which the second optical pathway 336 intersects the third optical pathway 327. However, in FIG. 3 where the second optical pathway 336 intersects the third optical pathway 327 at an approximately 90 degree angle, the partially reflective optical window 342 is oriented at approximately a 45 degree angle, e.g., relative to the direction of light travel through the second optical pathway 336. In particular, in the illustrated exemplary embodiment, the partially reflective optical window 342 is oriented at substantially 45° relative to the second 336 and third 327 optical pathways, as well as the first 320 and second 324 optical emitters. In this arrangement, the partially reflective optical window 342 is configured to reflect a portion of the light emitted by the first optical emitter 320 from the second optical pathway 336 into the third optical pathway 327, and to transmit at least a portion of light emitted by the second optical emitter 324 into the third optical pathway 327. The partially reflective optical window 342 shown in FIG. 3 can also act to transmit a portion of the light emitted from the first optical emitter 320 into the second optical pathway 336 toward the first optical pathway 326, and to reflect a portion of the light emitted from the second optical emitter 324 from the third optical pathway 327 into the second optical pathway 336 and toward the first optical pathway 326.

Figure 4:
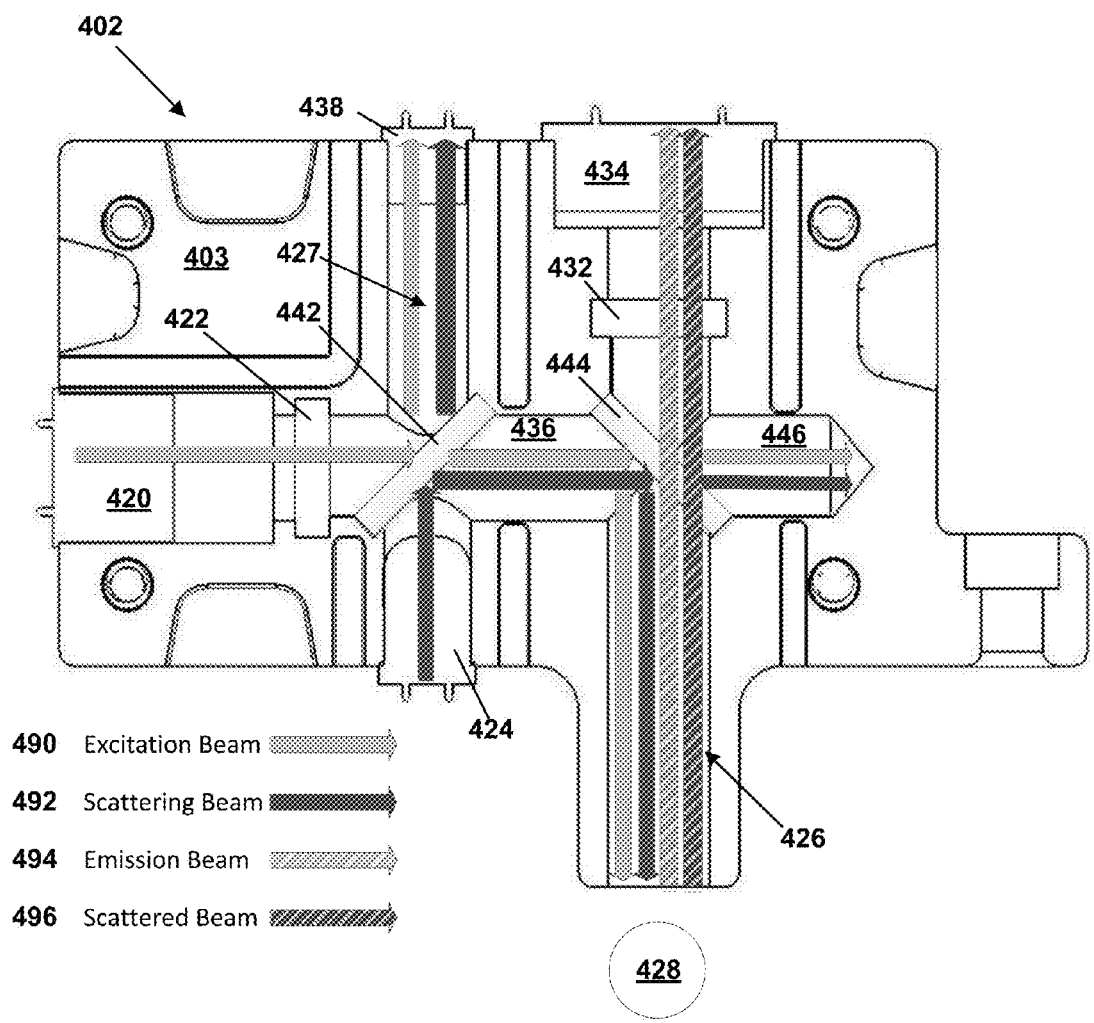
FIG. 4 is a conceptual diagram illustrating example light flows through the optical sensor of FIG. 3.

FIG. 4 is a conceptual diagram illustrating example light flows through the optical sensor illustrated in FIG. 3. For ease of description, FIG. 4 illustrates light emanating from a first optical emitter 420 and a second optical emitter 424 simultaneously and also light being received by a first optical detector 434 and a reference optical detector 438 simultaneously. In practice, the first optical emitter 420 and the second optical emitter 424 may emit at the same time or at different times. Further, the first optical detector 434 and the reference optical detector 438 may receive light while one or both of the first optical emitter 420 and the second optical emitter 424 are emitting or during a time period in which one or both of the emitters are not emitting light into the fluid sample under analysis. Therefore, although FIG. 4 illustrates various light flows as occurring simultaneously in sensor 402, it should be appreciated that an optical sensor according to the disclosure is not limited to such an example operation.

In the example of optical sensor 402, light is emitted from a first optical emitter 420 at a first wavelength into a second optical pathway 436. The light from the first optical emitter 420 may be configured to excite fluorescence in a fluid sample and will thus be referred to as generating an excitation beam 490 for purposes of illustration. Within sensor 402 in the example of FIG. 4, the excitation beam 490 is emitted into the second optical pathway 436 where it encounters a partially reflective optical window 442. A portion of the excitation beam 490 may be reflected by the partially reflective optical window 442 to be detected by a first reference optical detector 438. Another portion of the excitation beam 490 may pass through the partially reflective optical window 442 and continue traveling through the second optical pathway 436.

In operation, light is also emitted from a second optical emitter 424 at a second wavelength into a third optical pathway 427. The light from the second optical emitter 424 may be configured to scatter off the fluid sample and will thus be referred to as generating a scattering beam 492 for purposes of illustration. Within sensor 402 in the example of FIG. 4, the scattering beam 492 is emitted into the third optical pathway 427 where it encounters the partially reflective optical window 442. A portion of the scattering beam 492 may be reflected by the partially reflective optical window 442 toward the second optical pathway. Another portion of the scattering beam 492 may pass through the partially reflective optical window 442 and continue traveling through the third optical pathway 427 to be detected by the second optical detector 438, which may function as a reference optical detector.

Portions of the excitation beam 490 and the scattering beam 492 traveling through the second optical pathway 436 in the example of FIG. 4 encounter partially reflective optical window 444. A portion of the excitation beam 490 and the scattering beam 492 encountering the partially reflective optical window 444 may be reflected by the partially reflective optical window into the first optical pathway optical pathway 426. These beams reflected into the first optical pathway 426 are directed to the fluid sample under analysis via an optical lens 428 disposed between the first optical pathway and the fluid sample. In some examples, another portion of the excitation beam 490 and the scattering beam 492 encountering the partially reflective optical window 444 may pass through the partially reflective optical window into the beam dump 446. The beam dump 446 may be an optically absorbent region of optical sensor 402 positioned on an opposite side of the first optical pathway 426 from the second optical pathway 436. The beam dump may absorb light directed into the region, e.g., to help prevent the light from reflecting back into first optical pathway 426 and being detected by optical detector 434.

As previously described, the excitation beam 490 traveling into the fluid sample via optical lens 428 may excite fluorescence in the sample while the scattering beam 492 traveling into the fluid sample may scatter, e.g., by suspended materials in the sample such as oil or particulates. In some examples, the fluorescent light emitted by the fluid sample in response to the excitation beam 490 is at a third wavelength different from the wavelength or wavelengths encompassed by either the excitation beam 490 or the scattering beam 492. Depending on the fluid sample under analysis, the third wavelength may be in the UV or near-UV spectrum, such as in a range from approximately 285 nm to approximately 385 nm (e.g., a wavelength greater than 300 nm, such as 315 nm). Fluoresced light and scattered light can be captured by the optical lens 428 and directed back into the first optical pathway 426 of the sensor 402. In some embodiments, the optical lens 428 acts to substantially collimate the fluoresced and scattered light into an emission beam 494 and a scattered beam 496, respectively, which travel back through the optical pathway 426 toward the partially reflective optical window 444.

In the configuration of FIG. 4, the partially reflective optical window 444 may transmit at least a portion of the emission beam 494 generated by fluorescing molecules in the fluid sample under analysis and also at least a portion of the scattered beam 496 generated by light scattering caused by the fluid sample. The emission beam 494 and scattered beam 496 may enter optical sensor 402 via optical lens 428 and travel through the first optical pathway 426 before encountering partially reflective optical window 444. Upon impinging upon the partially reflective optical window 444, at least a portion of the emission beam 494 and scattered beam 496 may pass through the partially reflective optical window and be detected by optical detector 434.

In some embodiments, the partially reflective optical window 444 may transmit more light or wavelengths of light to the first optical detector 434 than is desired to optically characterize the fluid sample under analysis. For example, the partially reflective optical window 444 may allow some portion of the excitation beam 490 to pass therethrough, such that portions of the excitation beam 490 that reach and are scattered by the fluid sample may reach the first optical detector 434 and be detected as corresponding to fluorescent emissions emitted by the fluid sample. To help control the light received and detected by the optical detector 434, the optical sensor 402 may include an optical filter 432 disposed between the optical lens 428 and the first optical detector 434 to filter out undesired light. In the embodiment of FIG. 4, the optical filter 432 is positioned between the partially reflective optical window 444 and the first optical detector 434. In some embodiments, the optical filter 432 is designed to filter out substantially all wavelengths of light (and, in other examples, all wavelengths of light) emitted by the first optical emitter 420. This may help prevent light emitted by the first optical emitter 420 that does not generate fluorescent emissions from being detected by the optical detector 434 and characterized as fluorescent emissions (e.g., light from the first optical emitter 420 that travels toward the optical detector 434 rather than toward optical lens 428 and/or light from the optical emitter that scatters in the fluid sample rather than generates fluorescent emissions). The optical filter 432 may transmit substantially all (and, in other examples, all) wavelengths of fluorescent emissions emitted from the fluid sample in response to the light from the first optical emitter 420 and wavelengths of light scattered by the fluid sample in response to light from the second optical emitter 424.

The first optical detector 434 can be configured to detect or measure the intensity and/or other properties of incident light thereupon. As described, the first optical detector 434 may receive at least a portion of the scattered beam 496 and the emission beam 494 transmitted from the fluid sample through the partially reflective optical window 444. In some embodiments, such as that shown in FIG. 3, the first optical detector 434 can comprise a single detector configured to detect light from both the emission beam 494 and the scattered beam 496. In such an arrangement, optical sensor 402 may control the first optical emitter 420 and the second optical emitter 424 to alternatingly emit the excitation beam 490 and the scattering beam 492. Light detected by the optical detector 434 in response to light emitted by the first optical emitter 420 (e.g., when the second optical emitter 424 is not emitting light) can be attributed to fluorescent emissions generated in the fluid sample. Conversely, light detected by the optical detector 434 in response to light emitted by the second optical emitter 424 (e.g., when the first optical emitter 420 is not emitting light) can be attributed to light scattering caused by the fluid sample. In this way, a single detector can detect and resolve both the emission beam 494 and the scattered beam 496 propagating from the fluid sample under analysis.

As previously described, the first optical detector can detect light fluoresced from the fluid sample and received as at least one emission beam 494. In some embodiments, the intensity of the emission beam 494 can be measured to calculate a characteristic of the sample, for example the concentration of a fluorophore. In one example, the fluoresced light from the sample is measured while light from the first optical emitter 420 is emitting and incident on the fluid sample. In another example, the fluoresced light from the sample is received and measured after light from the first optical emitter 420 ceases emitting. In these examples, fluorescence emitted by the fluid sample may persist beyond the duration of emission from the first optical emitter 420. Accordingly, the first optical detector 434 may receive fluorescent emissions from the fluid sample subsequent to ceasing emission of light from the first optical emitter 420. In some examples, optical sensor 402 may determine a characteristic of the fluid sample under analysis based the magnitude of fluorescent emissions detected by the first optical detector 434 and the change in that magnitude over time after ceasing light emission by the first optical emitter 420. For example, the optical sensor 402 may perform time-resolved fluorescence spectroscopy by measuring a fluorescence decay curve (e.g., fluorescence intensity as a function of time) for the fluid sample. This may involve measuring fluorescent emissions emanation from the fluid sample under analysis from a time when the first optical emitter 420 ceases emitting light to a time when the first optical detector 434 ceases detecting fluorescent emissions from the fluid. In addition to detecting fluorescent emissions, light scattered off the fluid sample and returned to the sensor in the form of a scattered beam 496 can also be detected by optical detector 434.

In some examples, the amount of fluorescence emitted by the fluid sample under analysis is dependent upon the amount of excitation light directed into the sample by the first optical emitter 420. Likewise, the amount of light scattered by the fluid sample may be dependent upon the amount of scattering light directed into the sample by the second optical emitter 424. In such examples, the intensity of light emitted by the first optical emitter 420 and/or the second optical emitter 424 can be measured, e.g., by second optical detector 438. Optical sensor 402 can then adjust the magnitude of the fluorescent emissions and/or scattered light detected by the first optical detector 434 based on the magnitude of light emitted by the first optical emitter 420 and/or the second optical emitter 424.

In some circumstances, light emitted by the second optical emitter 324 in the configuration of FIG. 3, for example, can substantially flood optical pathways 326, 327, 336. In some such instances, light of the second wavelength within the housing 303 can interfere with the measurement of the light scattered off the fluid sample. That is, light travelling through various optical pathways can result in a measureable background signal at the optical detector 334. Too large of a background signal can obscure measurements within the system. For example, a large detected background signal of light of the second wavelength can make it difficult to accurately detect light scattered from the sample, especially in samples with minimal scattered light. Inaccuracy in measuring the scattered light can lead to a false measurement of the sample turbidity. An error in the turbidity measurement can manifest itself in an error in correcting the fluorometric measurement of a concentration, for example.

Figure 5:
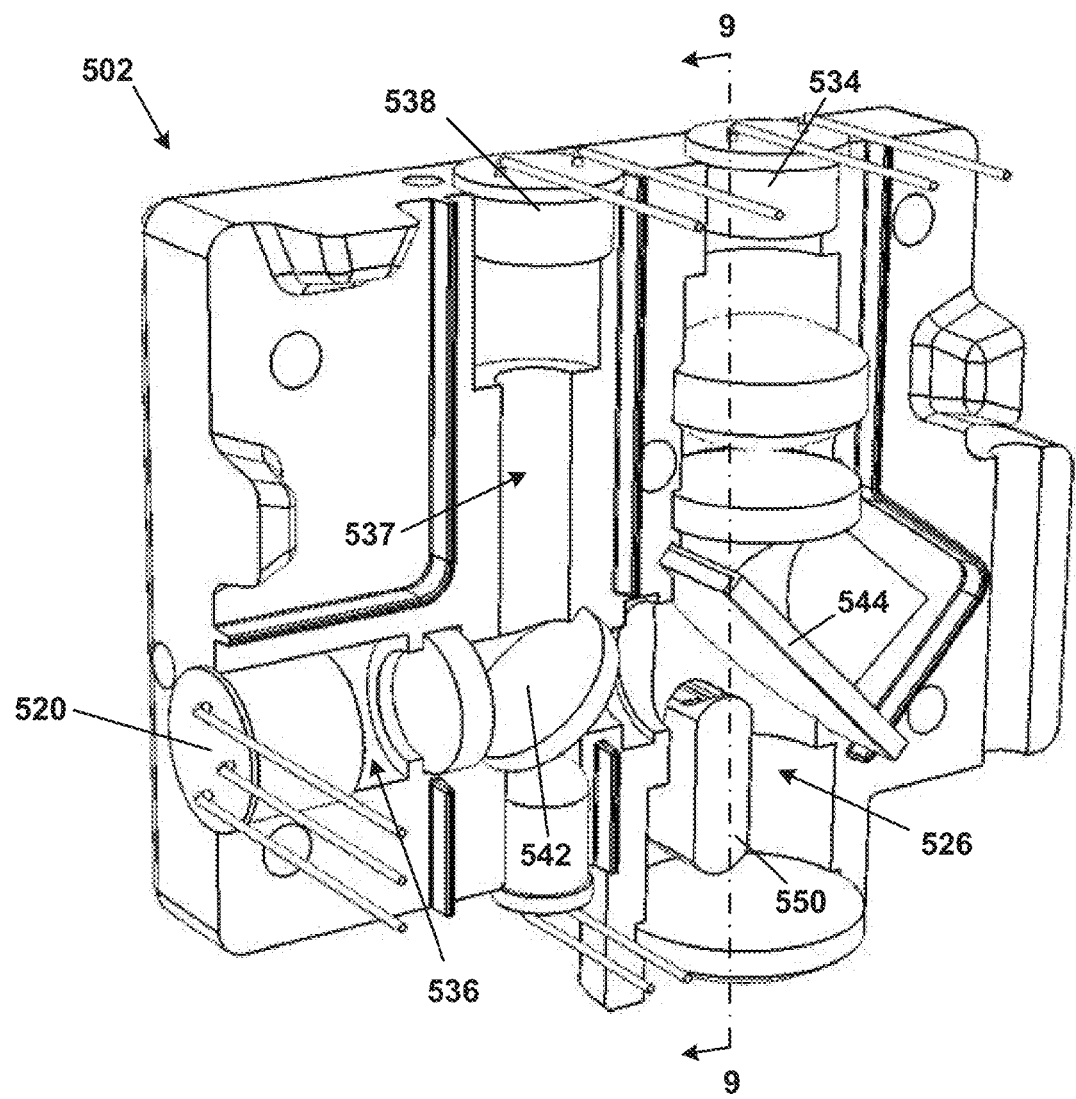
FIG. 5 is a cross-sectional view of an alternative embodiment of an optical sensor.

In some embodiments, components of the optical sensor can be repositioned to minimize or eliminate background light in the system. FIG. 5 is a cross-sectional view of an alternative embodiment of an optical sensor. The sensor 502 of FIG. 5 includes a first optical emitter 520, first 526, second 536 and third 537 optical pathways, partially reflective optical windows 542 and 544, first optical detector 534 and first reference optical detector 538 similar to the illustrated embodiments of FIGS. 3 and 4. Sensor 502 of the illustrated embodiment comprises an optical emitter assembly 550 disposed in the first optical pathway 526. The optical emitter assembly 550 can be configured to emit and/or detect light, and, in some embodiments, is configured to emit light of the second wavelength toward the fluid sample via the first optical pathway 526. The sensor 502 of FIG. 5 further includes a collimating lens 561 between the optical emitter assembly 550 and the sensor/sample interface (not shown). Collimating lens 561 can substantially collimate light from the optical emitter assembly 550 as the light passes therethrough prior to encountering the optical window and fluid sample (not shown).

Figure 7:
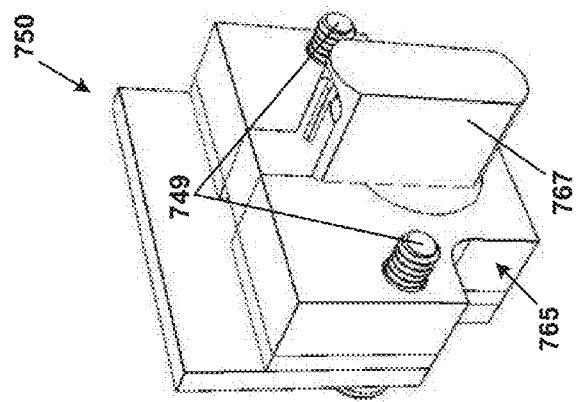
FIG. 7 is a perspective view of an embodiment of an optical emitter assembly which can be incorporated into the optical sensor of FIG. 6.
Figure 6:
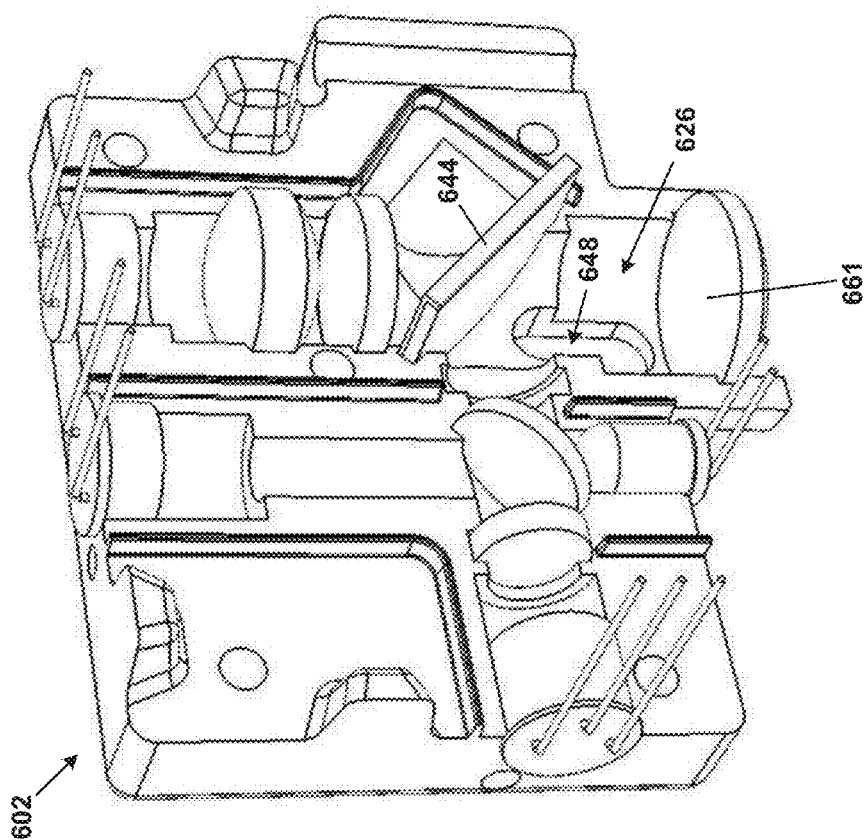
FIG. 6 is an embodiment of an optical sensor configured to receive an optical emitter assembly.

In some embodiments, the optical emitter assembly is removably attached to the sensor. FIGS. 6 and 7 illustrate a sensor for receiving an optical emitter assembly and the optical emitter assembly, respectively. The sensor 602 of FIG. 6 includes a hole 648 in the first optical pathway 626. Hole 648 can be configured to receive at least a portion of the optical emitter assembly therethrough. In the illustrated embodiment, the hole 648 is positioned between the partially reflective optical window 644 and the sensor/sample interface (not shown). The collimating lens 661 of the sensor 602 of FIG. 6 is positioned between the hole 648 and the sensor/sample interface such that when the optical emitter assembly is positioned through the hole 648, light emitted therefrom can be substantially collimated prior to encountering the fluid sample.

FIG. 7 is a perspective view of an optical emitter assembly according to some embodiments of the invention. As shown, optical emitter assembly 750 comprises an emitter housing 765 including a protrusion 767 extending therefrom. In some embodiments, the hole of the sensor is configured to receive protrusion 767. In the illustrated embodiment, assembly 750 includes a plurality of fasteners 749 for securing the optical emitter assembly 750 to the sensor. Fasteners 749 can include, for example, screws, bolts, or any other appropriate fastening component. Fasteners 749 can secure the optical emitter assembly 750 to the sensor housing such that the protrusion 767 extends at least partially into the hole in the housing.

Figure 8:
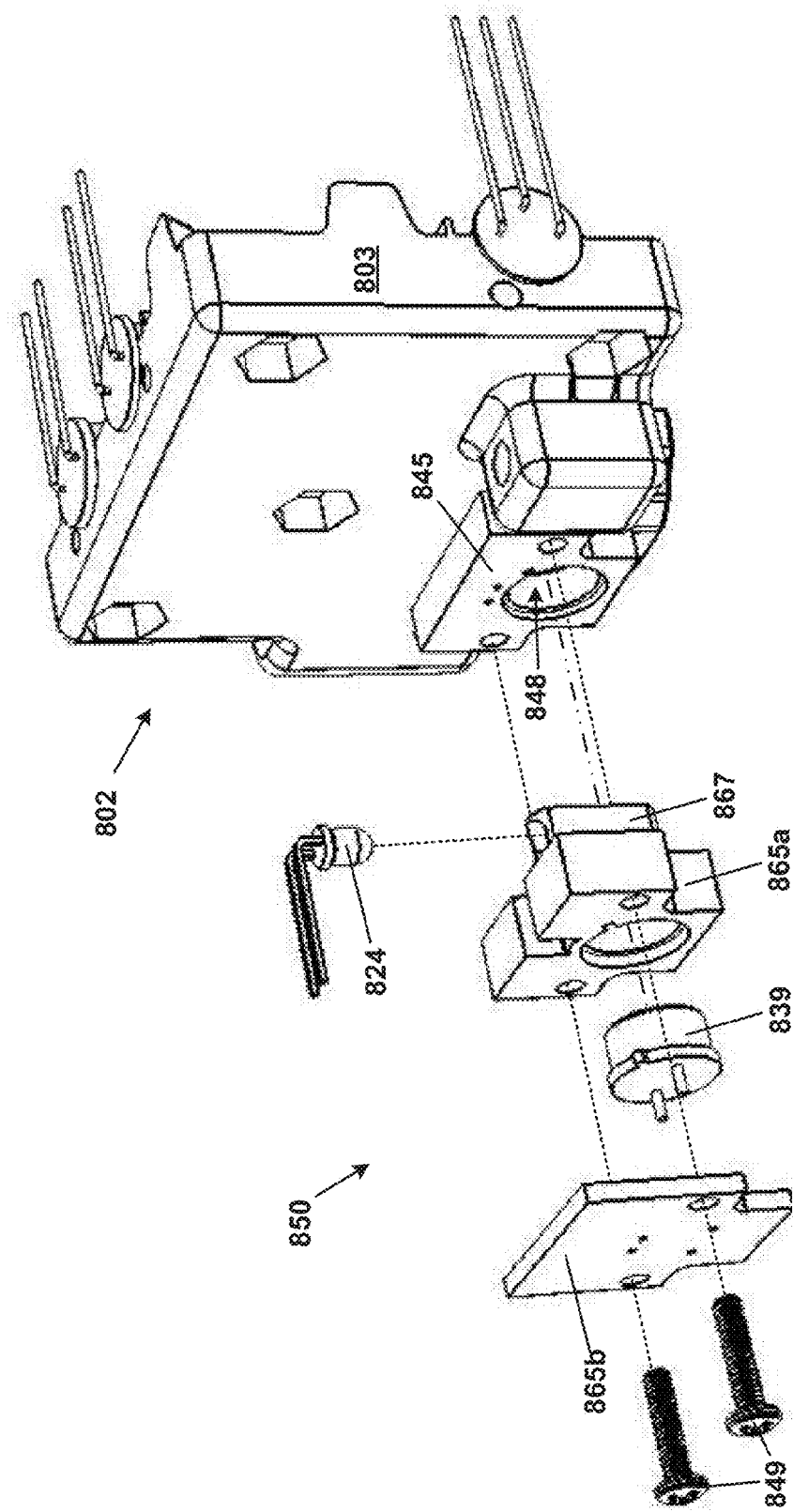
FIG. 8 is an exploded view illustrating the assembly of the optical emitter assembly and housing of the optical sensor.

FIG. 8 is an exploded view illustrating the assembly of the optical emitter assembly and housing of the optical sensor. As shown in the exploded view, the optical emitter assembly 850 can include the second optical emitter 824 and a second reference optical detector 839 configured to receive emissions from the second optical emitter 824. The second optical emitter 824 and second reference optical detector 839 can be positioned in housing 865a of the optical emitter assembly 850 as shown. In some embodiments, the housing 865a is closed off by a back plate 865b. Back plate 865b can comprise, for example a circuit board for interfacing with the second optical emitter 824 and second reference optical detector 839. In some embodiments, the optical emitter assembly 850 can be removably attached to the sensor housing 803.

The optical emitter assembly 850 can be held together and to the housing 803 of the optical sensor 802 via fasteners 849. The optical emitter assembly 850 can engage the housing 803 proximate a hole 848 through which a protrusion 867 at least partially extends. As shown, protrusion 867 can be configured to receive the second optical emitter 824 such that the second optical emitter 824 can emit light into the housing 803 of the optical sensor 802. In some embodiments, the hole 848 can be positioned in a receiving element 845 of the optical sensor 802 configured to receive the optical emitter assembly 850.

Figure 9:
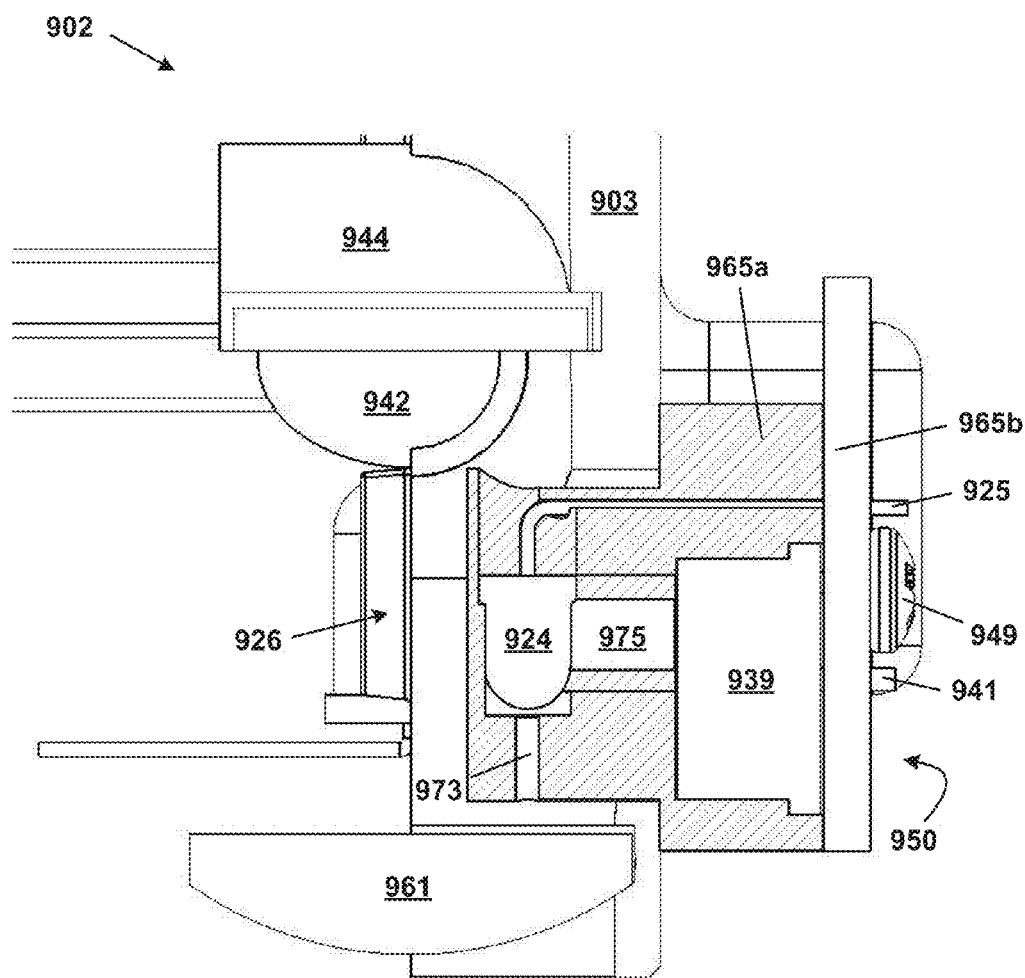
FIG. 9 is a cross-sectional view of an optical sensor and attached optical emitter assembly taken along the first optical pathway and line 9-9 in FIG. 5.

FIG. 9 is a cross-sectional view of an optical sensor and attached optical emitter assembly taken along the first optical pathway along line 9-9 in FIG. 5. As shown, the optical emitter assembly 950 is secured to the housing 903 of the optical sensor 902 via fastener 949. As previously discussed, the optical emitter assembly 950 is positioned such that the second optical emitter 924 is within the first optical pathway 926 of the sensor 902 between the partially reflective optical window 944 and the collimating lens 961. In the illustrated embodiment, the second optical emitter 924 is enclosed within the housing 965a of the optical emitter assembly 950. In some embodiments, the housing 965a of the optical emitter assembly 950 defines a plurality of pathways. As shown, the housing 965a defines a second emitter pathway 973 designed to direct light from the second optical emitter 924 toward the collimating lens 961 and subsequently the fluid sample. The housing 965a can define a second emitter reference pathway 975 designed to direct light from the second optical emitter 924 toward the second reference optical detector 939. In the illustrated embodiment, the housing 965a of the optical emitter assembly 950 otherwise encloses the second optical emitter 924, thereby preventing light from the second optical emitter 924 from undesirably emitting stray light into the optical pathways of the optical sensor. The housing 965a can additionally reduce the amount of stray light that reaches the second reference optical detector 939, which can result in a more accurate reference measurement of the light emitted from the second optical emitter 924.

It will be appreciated that many configurations which prevent light from the second optical emitter 924 from undesirably flooding the sensor. For example, the sensor 902 and/or optical emitter assembly 950 can include one or more optical shields disposed between the second optical emitter 924 and the optical detector (e.g., 534 in FIG. 5). In some embodiments, the shield(s) can be disposed between the second optical emitter 924 and the partially reflective optical window 944. In some instances, the one or more shields comprises the housing 965a of the optical emitter assembly 950 acting to prevent light from being emitted from the second optical emitter toward the optical detector. The shield(s) can comprise a substantially enclosed volume such as the housing 965a to prevent light from being emitted from the second optical emitter 924 toward the optical detector 934. One or more shields can act to substantially prevent light from being emitted from the second optical emitter toward the first optical detector through the first optical pathway. That is, while a portion of light emitted by the second optical emitter may initially be emitted toward the first optical detector, such a portion of the light prevented from reaching the first optical detector by the one or more shields.

In some embodiments the optical emitter assembly 950 includes a back plate 965b which can further act to define the substantially enclosed volume. Back plate 965b can combine with housing 965a to enclose one or both of the second optical emitter 924 and the second reference optical detector 939. In some embodiments, the back plate 965b can comprise a circuit board for interfacing with one or both of the second optical emitter 924 and the second reference optical detector 939. In the illustrated embodiment, back plate 965b is shown as having conductors 925 and 941 passing therethrough for electrically interfacing with the second optical emitter 924 and the second reference optical detector 939, respectively.

Figure 10A:
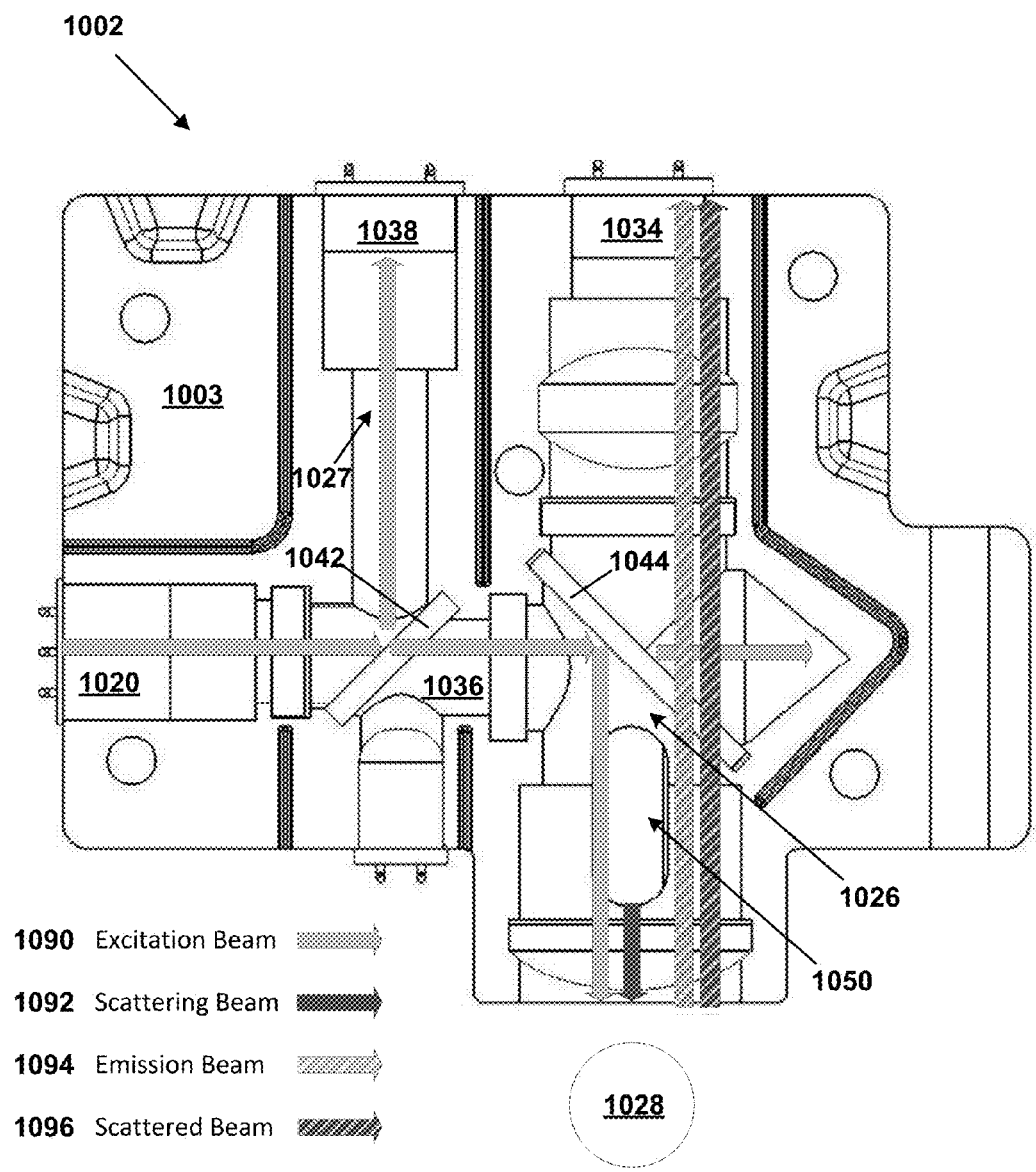
FIG. 10A is a conceptual diagrams illustrating example light flows through the optical sensor of FIG. 6.
Figure 10B:
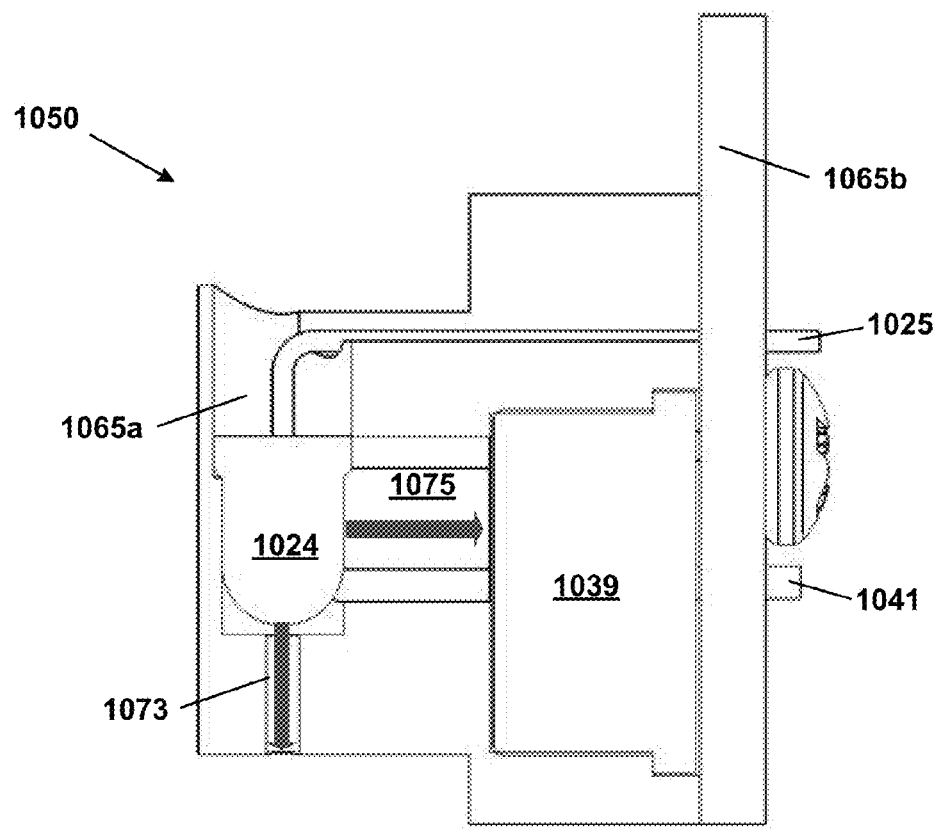
FIG. 10B is a conceptual diagrams illustrating example light flows through the optical emitter assembly of FIG. 7.

FIGS. 10A and 10B are conceptual diagrams illustrating example light flows through the optical sensor of FIG. 6. As shown in and described above with reference to FIG. 4, a first optical emitter 1020 is configured to emit light of a first wavelength, also referred to as the excitation beam 1090. The excitation beam 1090 is emitted into the second optical pathway 1036 where it encounters a partially reflective optical window 1042 which reflects a portion of the excitation beam 1090 toward a first reference optical detector 1038. Another portion of the excitation beam 1090 is transmitted through the partially reflective optical window 1042 to a second partially reflective optical window 1044, which reflects a portion of the excitation beam 1090 into the first optical pathway 1026 and toward the optical window 1028 and fluid sample (not shown). In some configurations, while propagating through the first optical pathway 1026 toward the fluid sample, a portion of the excitation beam can encounter an optical emitter assembly 1050 in the optical pathway 1026. In some embodiments, the optical emitter assembly 1050 blocks a portion of the excitation beam from reaching the optical window 1028.

As discussed elsewhere herein, the excitation beam 1090 can excite fluorescence in the fluid sample, which can enter the sensor 1002 via the optical window 1028 as an emission beam 1094. The emission beam 1094 can travel through the optical pathway 1026 to the optical detector 1034 where it can be analyzed. Since the intensity of fluorescent emissions measured as the excitation beam can depend on the intensity of the excitation beam exciting the emissions, the measured emission beam 1094 can be compared to the measured portion of the excitation beam 1090 at the first reference optical detector 1038. The comparison can be used to provide information about the fluid sample such as the concentration of a fluorophore.

In some embodiments, the optical emitter assembly 1050 is configured to emit light of a second wavelength, which can be referred to as the scattering beam 1092. The scattering beam 1092 can be directed from the optical emitter assembly 1050 and toward the fluid sample via the optical pathway 1026, collimating lens 1061 and optical window 1028. The scattering beam 1092 can subsequently scatter off of the sample. A portion of the scattered light can be received by the optical window and directed back into the optical pathway 1026 as a scattered beam 1096. The scattered beam 1096 can propagate through the optical pathway 1026 to the detector 1034 for analysis. The measured scattered beam 1096 can be used to determine, for example, the turbidity of the fluid sample. The turbidity can have an effect on the fluorescence of the fluid sample, and therefore can be measured and used to correct the fluorometry measurement and thus the concentration measurement based thereon.

The light flow of the scattering beam according to some embodiments is illustrated in FIG. 10B. According to the illustrated embodiment, the second optical emitter 1024 is substantially enclosed by housing 1065a of the optical emitter assembly. Substantially enclosed, as used herein, is intended to indicate that the housing encloses the optical emitter such that light emitted therefrom only escapes the housing via preconfigured pathways. The housing defines a second emitter pathway 1073 and a second emitter reference pathway 1075 through which light emitted from the second optical emitter 1024 (i.e., the scattering beam 1092) can propagate. For example, the scattering beam can propagate through the second emitter pathway 1073 out of the housing 1065a and the optical emitter assembly 1050 and toward the fluid sample as shown in FIG. 10A. The scattering beam 1092 can scatter off the sample and back into the sensor 1002 as a scattered beam 1096 and detected by detector 1034 as previously described.

As mentioned, a measurement of the scattered beam can provide information regarding the turbidity of the sample, which can be used to correct a fluorometry measurement. However, in some configurations, the measurement of the scattered beam 1096 is dependent not only on the turbidity of the sample, but also on the intensity of the scattering beam 1092. Accordingly, as shown in FIG. 10B, the housing 1065a of the optical emitter assembly 1050 includes a second emitter reference pathway 1075 via which light from the second optical emitter 1024 is directed toward a second reference optical detector 1039. The second reference optical detector 1039 can determine the intensity of the light emitted by the second optical emitter 1024. Such a measurement can be compared to the detected scattered beam 1096 to more accurately determine the turbidity of the sample.

Providing the second optical emitter 1024 and the second reference optical detector 1039 in the optical emitter assembly 1050 can act to reduce undesired light from entering the optical pathways of the optical sensor. For example, the housing 1065a of FIG. 10B allows light emitted from the second optical emitter 1024 to exit the housing 1065a as a scattering beam 1092 only via the second emitter pathway 1073 toward the fluid sample. Additionally, the housing 1065a of FIG. 10B is configured such that the second reference optical detector 1039 receives light via only the second emitter reference pathway 1075. Accordingly, the second reference optical detector 1039 receives light from only the second optical emitter 1024, reducing the noise received by the second reference optical detector 1039.

In addition, emitting light directly from the second optical emitter 1024 toward the fluid sample via second emitter pathway 1073 can result in a relatively intense scattering beam 1092 at the fluid sample. By comparison, in a configuration such as that in FIG. 4, the scattering beam 496 is potentially split by partially reflective optical windows 442 and 444 and only a portion of the emitted light is directed to the fluid sample. Thus, in a configuration such as is shown in FIG. 10B, the relative intensity of the light directed to the fluid sample can be larger when compared to other configurations. In some situations, the relative intensity of the light received.

Accordingly, in some configurations, emitting a scattering beam 1092 toward the sample from the optical emitter assembly 1050 disposed in the first optical pathway 1026 can improve the signal strength of the scattering 1092 beam to the sample and thus the scattered beam 1096. Additionally, positioning the second reference optical detector 1039 in the housing 1065a of the optical emitter assembly 1050 can result in a reduction of noise detected at the second reference optical detector 1039. In some situations, such a configuration can lead to improved accuracy in determining the turbidity of the fluid sample. An improved measurement of the sample turbidity can increase the accuracy of the turbidity correction in determining a concentration from measured fluorescence as previously discussed.

Optical sensors in accordance with the disclosure can be used as part of a system (e.g., fluid system 100 in FIG. 1) in which the sensor is communicatively coupled to a controller to receive data from and send data to the sensor. The controller may include an integral component such as a microcontroller, or an external component, such as a computer. The controller can be in communication with the first and second optical emitters, as well as various optical detectors. The controller can be configured to control the first and second optical emitters to emit light at a first wavelength and a second wavelength, respectively. As discussed, the first wavelength may excite fluorescence in a fluid sample, while the second wavelength may scatter off of the fluid sample. The controller can also be configured to control an optical detector to detect fluorescent emissions emitted by the fluid sample and also light scattered by the sample. The controller can be further configured to determine at least one characteristic of the fluid sample based on the detected fluorescent emissions. For example, the controller may determine a characteristic of the fluid sample based on data generated by the optical sensor and information stored in a memory associated with the controller, such as calculating based on an equation, finding in a lookup table, or any other method known in the art.

In some embodiments, the controller can be further configured to adjust the determination of the at least one characteristic based on one or more additional measurements. For example, the controller can adjust the determination of the at least one characteristic based on a measured turbidity of the sample, which can be determined from detected light scattered off the sample. Further, the controller can be configured to detect light emitted from optical emitters via one or more reference optical detectors to establish reference measurements. The controller can compare the detected light from the sample to light detected at the one or more reference optical detectors to determine a relative measurement which can be used in determining the at least one characteristic.

In some examples, a first light source directs light to a first reference optical detector and to the fluid sample, where it causes fluorescence which is detected by a first optical detector. A second light source can be configured to direct light to a second reference optical detector and to the fluid sample, where it at least partially scatters off of the fluid sample and is detected at a second optical detector. The controller can be configured to compare the detected light at the first optical detector and the detected light at the first reference optical detector to determine a relative fluorescence measurement. Similarly, the controller can compare the detected light at the second optical detector and the second reference optical detector to determine a relative turbidity measurement. In such a configuration, the controller can determine the at least one characteristic of the fluid sample based on a combination of the relative fluorescence measurement and the relative turbidity measurement.

In applications where the first and second optical emitters are operated in an alternating sequence of activation, the controller can coordinate the frequency and duration of light emissions from each optical emitter. In addition, in embodiments where the sensor includes one or more reference optical detectors, the controller can detect light from the first and second optical emitters and use this detected light to calibrate light detected by the first optical detector.

In some examples, an optical sensor according to the disclosure also includes one or more non-optical sensors. Exemplary non-optical sensors can include, but are not limited to, pH sensors, conductivity sensors, and temperature sensors. Data from the non-optical sensors can be used determine non-optical characteristics of the sample under analysis. In some embodiments, data from one or more non-optical sensors can be used to adjust a measurement of fluorescent emissions from a fluid sample to determine one or more characteristics of the sample. For example, a temperature sensor can be mounted in a sensor body to correct for temperature effects on fluorescence as well as on electronics and/or detectors. In other examples, data from a non-optical sensor may be used to monitor a fluid sample and/or control a fluid process in addition to or in lieu of using optical sensor data to monitor the fluid sample and/or control the fluid process.

As discussed, in certain embodiments, an optical sensor according to the disclosure may detect light fluoresced from a sample at one or more wavelengths and scattered off of the sample at yet another wavelength. The optical sensor may also detect additional characteristics, such as non-optical characteristics, of the fluid sample. Data generated by the optical sensor can be used to calculate or otherwise determine at least one characteristic of the sample. Such data can be received simultaneously, alternatingly in sequence, or in a combination in which some but not all data can be received simultaneously.

The received data contributing to determining at least one characteristic can be received in a plurality of channels. Channels can be optical channels, comprising one or more fluorescence channels and a scattering channel, but can also include data channels such as data received from one or more non-optical sensors. Optical channels can be defined by wavelength bands, for example. Accordingly, in some embodiments, data is received in the form of a first fluoresced wavelength is data received in the first fluorescent channel, while data received in the form of light scattered off the sample is data received in the scattering channel. Thus, in various embodiments, the optical sensor can receive data in any combination of optical channels via the first optical pathway simultaneously and/or alternatingly, and additionally in non-optical channels from one or more non-optical sensors. In addition, as previously described, the first or second reference optical detectors can receive light from the first or second optical emitters used for calibration of measurements at the first optical detector. Thus, the data received at the reference optical detectors can be received in one or more calibration channels. In some examples, the first and second reference optical detectors can be connected electrically in parallel. In such an embodiment, each of the first and second reference optical detectors can provide reference signals in a single reference channel.

In applications where the optical sensor includes a single optical detector that detects fluorescent emissions received from the fluid sample and also detects scattered light received from the fluid sample, the first and second optical emitters may activate and deactivate in alternating sequence. This may allow data generated by the optical detector to be resolved into fluorescent emission data corresponding to detected fluorescent emissions and scattering data corresponding to detected scattered light. In other examples, the optical sensor can include multiple optical detectors that detect fluorescent emissions received from the fluid sample and detect scattered light received from the fluid sample. For example, the optical sensor may include one optical detector that detects fluorescent emissions received from the fluid sample and another optical detector that detects scattered light received from the fluid sample.

Figures 11A, 11B:
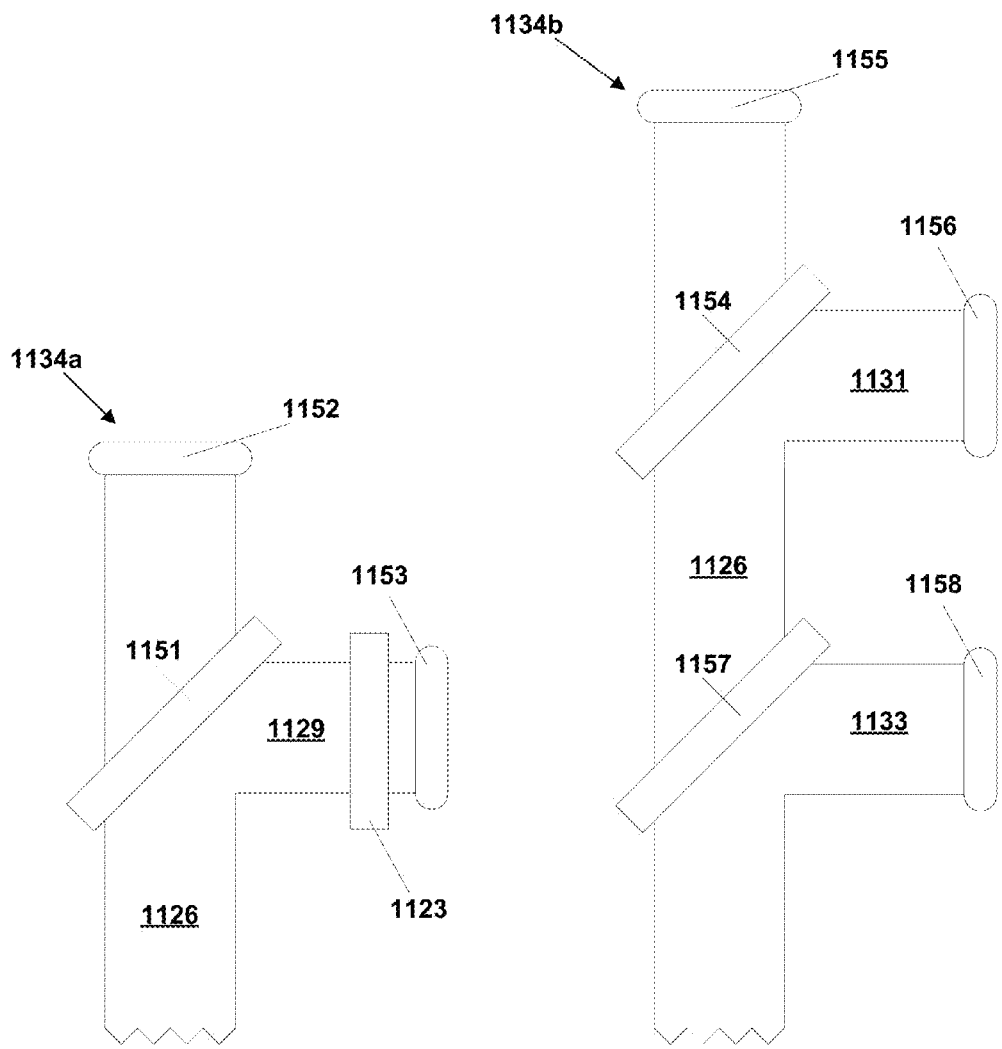
FIGS. 11A and 11B illustrate example optical detector arrangements that may be used in an optical sensor such as that of FIG. 2.
Figure 12A:
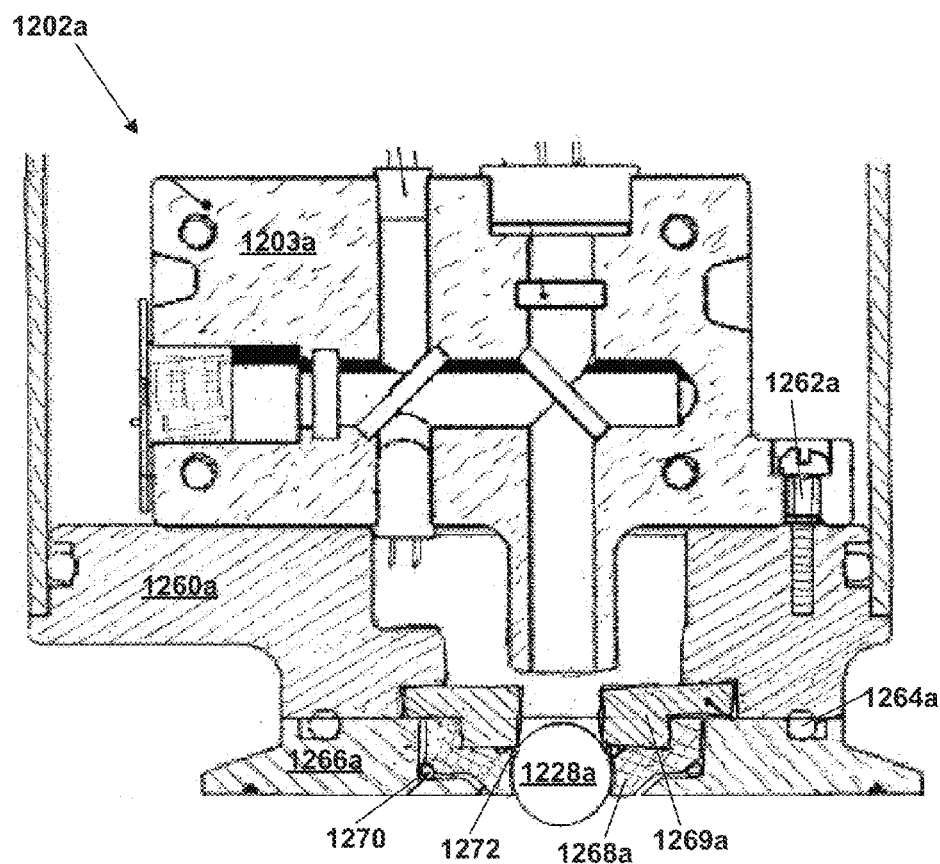
FIGS. 12A-12D illustrate example optical sensor housing and component arrangements that may be used for an optical sensor such as that of FIG. 2.
Figure 12B:
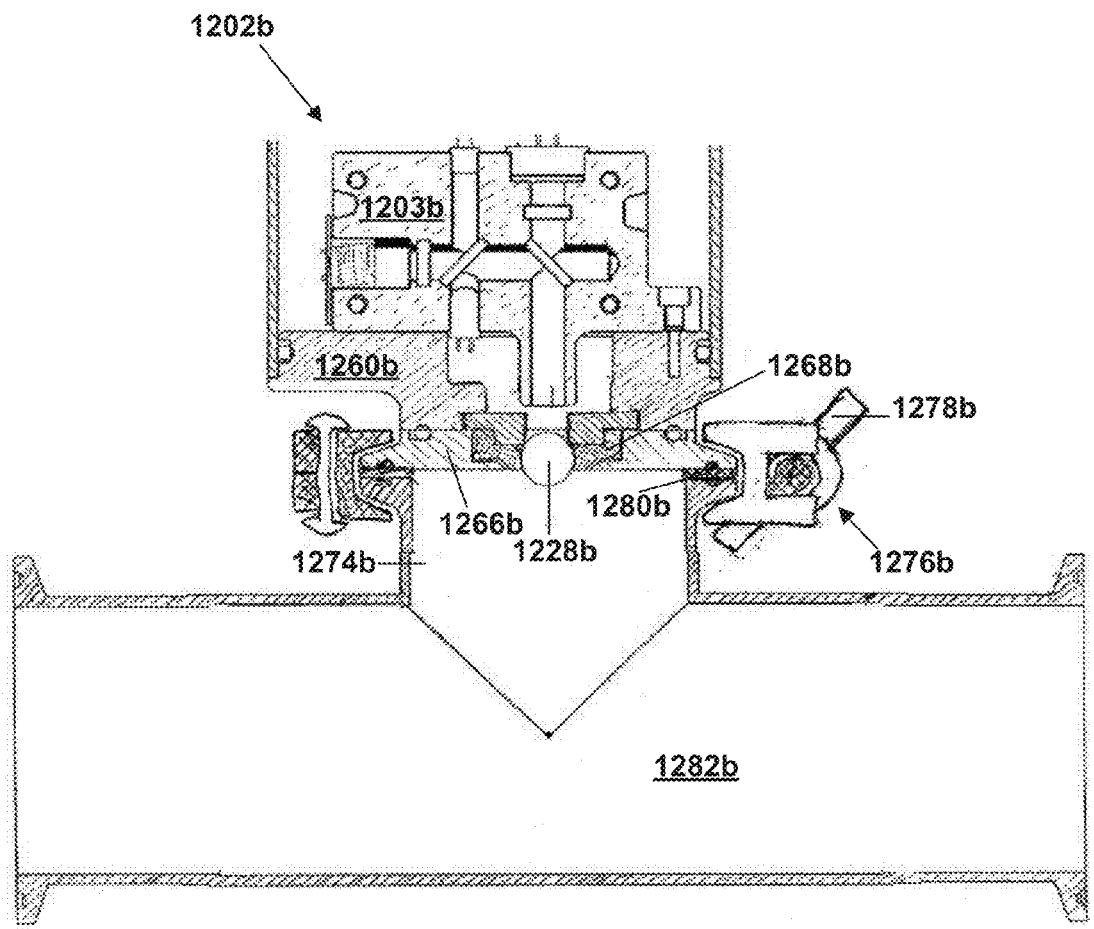
Figure 12C:
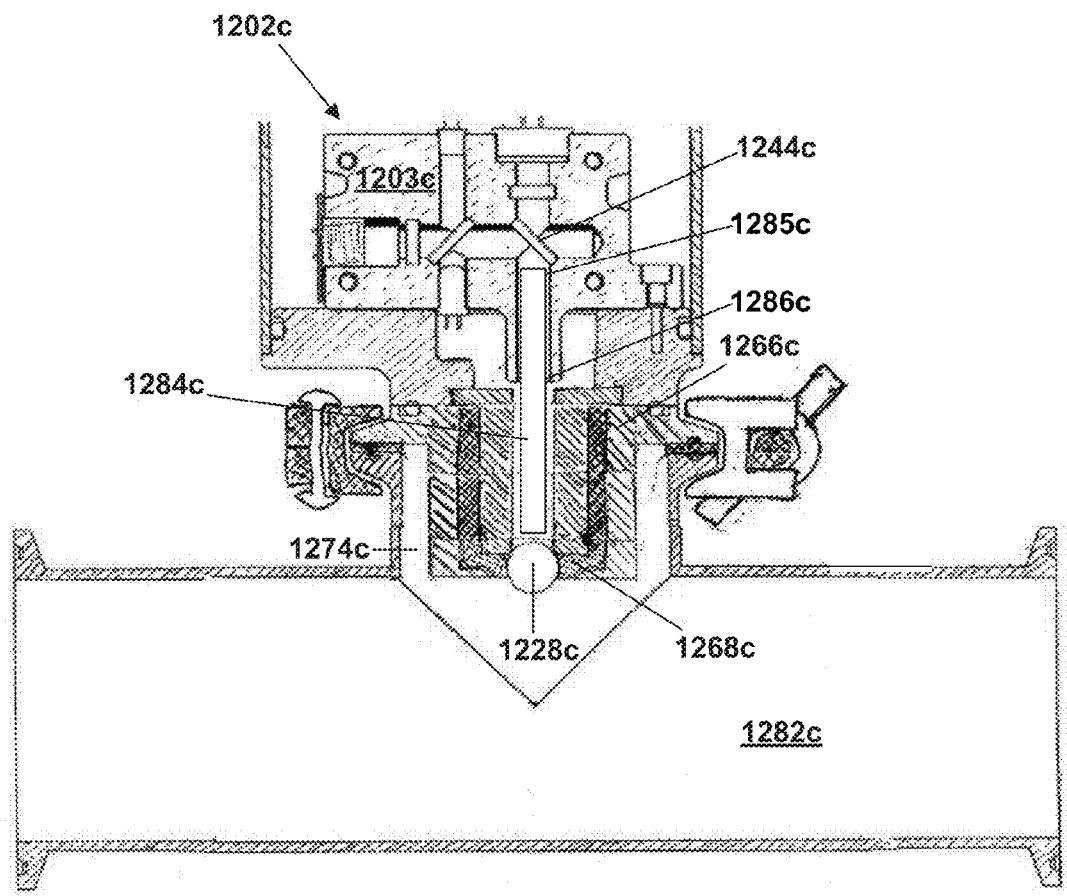
Figure 12D:
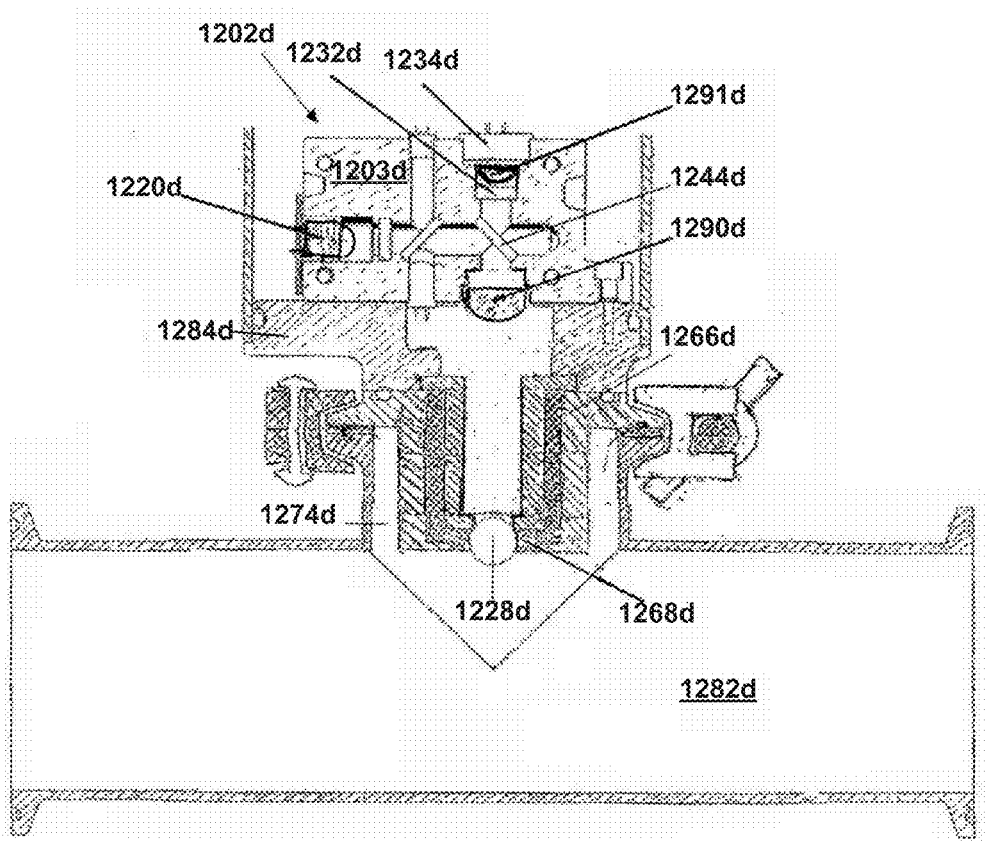

As further described in U.S. patent application Ser. No. 14/039,683, which is incorporated by reference, FIGS. 11A and 11B illustrate example alternative optical detector arrangements that can be used in an optical sensor, such as the optical sensors of FIGS. 2-10. In general, FIGS. 5A and 5B illustrate various configurations for incorporating a plurality of optical detector elements (e.g., 1152, 1153, 1155, 1156, 1157) into an optical pathway 1126. As described in the incorporated application and similarly to other configurations described elsewhere herein, partially reflective optical widows (e.g., 1151, 1154, 1157) and optical filters (e.g., 1123) can be used to filter, separate, and direct light to appropriate optical detector elements. For example, fluoresced light and scattered light may be directed to separate optical detector elements by a partially reflective optical window in order to measure fluoresced and scattered light simultaneously. Many different configurations are possible and are within the scope of the disclosure. As further described in U.S. patent application Ser. No. 14/039,683, which is incorporated by reference, an optical sensor according to the disclosure can be modified to meet requirements for use in specific applications or configurations. For example, FIGS. 12A-12D (FIGS. 6A-6D of the incorporated application) illustrate a sensor attached to various components for use with a fluid vessel. Such figures also illustrate different sensor components and physical arrangements that can be used by any sensor according to the disclosure. As described in the incorporated application, various sensor arrangements can be implemented without departing from the scope of the invention. Further, Embodiments of the invention can be fitted into various fluid containers by way of mounting discs, press-fit inserts, flanges and the like.

Figure 13:
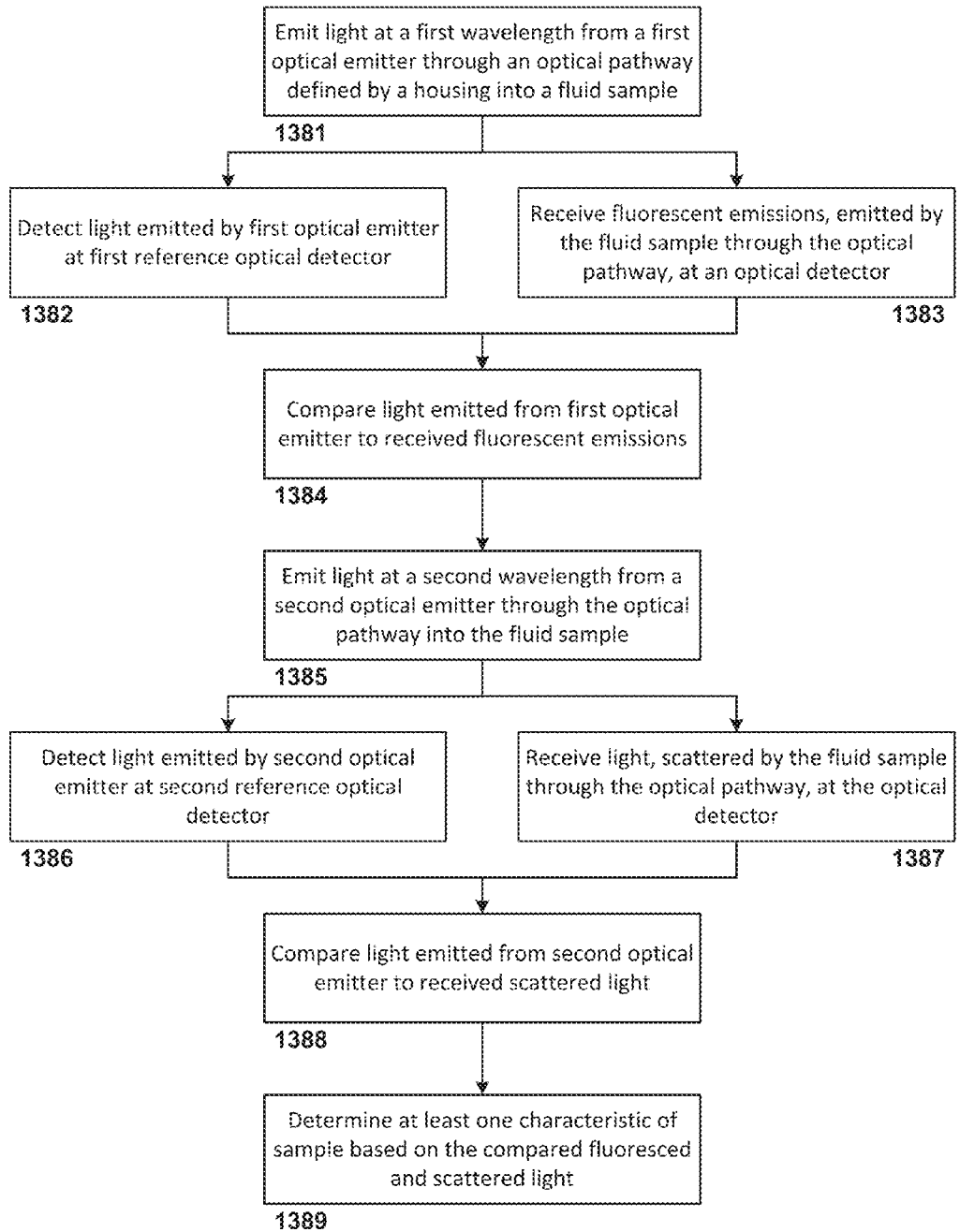
FIG. 13 is a process flow diagram illustrating exemplary operation of a sensor.

Various embodiments and configurations of sensors have been described. FIG. 13 is a process flow diagram of an optical analysis technique according to the disclosure. FIG. 13 illustrates a process in which a sensor emits light at a first wavelength 1381 from a first optical emitter through an optical pathway and into a fluid sample. The optical pathway is defined by a housing of the sensor. The sensor is configured to detect 1382 light emitted by the first optical emitter at a first reference optical detector. In some embodiments, the fluorescent emissions are excited by the light emitted by the first optical emitter. Thus, in some configurations, the sensor also receives fluorescent emissions 1383 emitted by the fluid sample through the optical pathway at an optical detector. The sensor can compare 1384 the light emitted from the first optical emitter to the received fluorescent emissions. The comparison can provide information regarding the amount of fluoresced light relative to the intensity of light of the first wavelength incident on the sample. In some examples, the comparison can be performed in order to determine a relative fluorescence measurement.

The sensor can be configured to emit light at a second wavelength 1385 from a second optical emitter, through the optical pathway and into the fluid sample. In some configurations, the light of the second wavelength is directed to the sample via the same optical pathway as light of the first wavelength. The sensor can detect 1386 light emitted at the second wavelength at a second reference optical detector. The sensor can also receive light, scattered by the fluid sample 1387 through the optical pathway, at the optical detector. Similar to the process referenced above with light of the first wavelength, the sensor can compare 1388 the light emitted from the second optical emitter to the received scattered light. The comparison can provide information regarding the amount of scattered light relative to the intensity of light of the second wavelength incident on the sample. In some examples, the comparison can be performed in order to determine a relative turbidity measurement.

In some embodiments, the sensor can be configured to determine 1389 at least one characteristic of the sample based on the compared fluoresced and scattered light. In some examples, the sensor can determine the concentration of a constituent of the fluid sample. For example, in some instances, the relative fluorescence measurement from the fluid sample is indicative of the concentration of a fluorophore in the sample. However, in some situations, the turbidity of the sample can have an effect on the fluorescent properties of the sample. The relative turbidity measurement can be used to determine the turbidity of the sample. Thus, in some examples, the compared scattered light indicative of the turbidity can be used to adjust a determination of a fluorophore concentration based on the compared fluoresced light. In general, the relative fluorescence measurement and the relative turbidity measurement can be combined in order to determine at least one characteristic of the fluid sample.

It will be appreciated that various steps can be added, omitted, permuted or performed simultaneously with regard to the method of FIG. 13. For example, as described in the process of FIG. 13, light is emitted at the first wavelength and second wavelength into a fluid sample, as well as received from the fluid sample, via a single optical pathway. Received light can be scattered off the sample, and in some embodiments, comprises light of the second wavelength scattered off the sample. Received light can also be in the form of light fluoresced from the sample, which can be caused by the light of the first wavelengths. As discussed previously, in some embodiments, the sensor is unable to resolve the difference in light scattered by the sample and fluoresced from the sample if they are simultaneously incident on the optical detector. Thus, in some embodiments, emitting light at the first wavelength is ceased prior to emitting light at the second wavelength 1385. For the same reason, should the process be repeated, in some embodiments, emitting light at the second wavelength is ceased prior to emitting light at the first wavelength 1381.

In further embodiments, emitting light at the first wavelength is ceased prior to receiving useful fluorescent emissions at the optical detector. This can be done, for example, if a sample contains multiple fluorescing species that fluoresce for different durations, such that the fluorescence from one species persists longer than that from another species. If fluorescence from the longer persisting species is desired to be measured while fluorescence from the shorter persisting species is extraneous, it can be advantageous to cease emitting light at the first wavelength, wait for the fluorescence excited by the shorter persisting species to subside, and then measure the remaining fluorescent emissions attributable to the longer persisting species. It should be noted that the optical detector may be receiving fluorescent emissions from the sample while light of the first wavelength is being emitted; however, the measurement of fluoresced light may or may not be disregarded until the appropriate time.

It will be appreciated that the process outlined in FIG. 13 can be performed by a controller in a system comprising a sensor. The controller can include a processor for controlling the timing and duration of emitting light from either the first or second optical emitters, as well as the timing of receiving light from the fluid sample. That is, the controller can be programmed to disregard received light when there is extraneous light present that can disrupt the ability to adequately determine the at least one characteristic of the sample. The controller can utilize data from received fluoresced light, scattered light, and any other data that it receives to calculate or otherwise determine, or adjust the determination of, at least one characteristic of the sample.

Exemplary sensors have been described. Some embodiments comprise multi-channel fluorometric sensors in which fluorescence from a sample is excited and detected in at least one fluorescence channel, and the detected fluorescence is used to determine a characteristic of the sample. Other factors, such as light scattered off the sample, or additional non-optical measurements can be used to supplement the fluorescence detection and account for potential variations in fluorescence of the sample. The sensor can be part of a system comprising a controller to automate the control of emitters and detectors, and calculate or otherwise determine characteristics of the sample from measured data. Sensors can be secured into vessels in which fluid samples to be characterized are present or flow through.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "controller" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following example may provide additional details about an optical sensor in a system used to determine concentrations of components within a fluid sample.

The invention claimed is:

1. An optical sensor comprising:
   a first optical detector;
   an optical window;
   a first optical pathway extending between the first optical detector and the optical window;
   a first optical emitter and configured to emit light at a first wavelength;
   an optical emitter assembly at least partially disposed in the first optical pathway, the optical emitter assembly comprising a second optical emitter configured to emit light at a second wavelength into the first optical pathway and toward the optical window; and
   a housing including the first optical pathway and supporting the first optical detector, the optical window, the first optical emitter, and the optical emitter assembly; wherein
   light emitted from the first optical emitter is directed from the housing into a fluid sample via at least part of the first optical pathway and via the optical window; and
   light is received from the fluid sample into the housing and directed to the first optical detector via the optical window and the at least part of the first optical pathway.

2. The sensor of claim 1, wherein the optical emitter assembly in the first optical pathway blocks a portion of light from the first optical emitter from reaching the optical window.

3. The sensor of claim 1, further comprising
   a first reference optical detector configured to receive at least a portion of the light emitted from the first optical emitter; and
   a second reference optical detector configured to receive at least a portion of the light emitted from the second optical emitter, the second reference optical detector positioned in the optical emitter assembly.

4. The sensor of claim 3, wherein the optical emitter assembly further comprises a shield for substantially preventing light from being emitted from the second optical emitter toward the first optical detector through the first optical pathway.

5. The sensor of claim 4, wherein the optical emitter assembly is removably coupled to the optical sensor.

6. The sensor of claim 4, wherein the shield comprises a substantially enclosed volume.

7. The sensor of claim 6, wherein the second optical emitter is configured to emit light of the second wavelength into the substantially enclosed volume; and the second reference optical detector is disposed within the substantially enclosed volume.

8. The sensor of claim 1, further comprising a collimating lens disposed between the second optical emitter and the optical window and configured to substantially collimate the light emitted from the second optical emitter toward the optical window.

9. The sensor of claim 1, further comprising a second optical pathway intersecting the first optical pathway at an approximately 90 degree angle, and wherein the first optical emitter is configured to emit light into the second optical pathway.

10. The sensor of claim 9, further comprising a first partially reflective optical window positioned at an intersection between the first optical pathway and the second optical pathway and configured to direct at least a portion of light emitted by the first optical emitter into the first optical pathway and toward the fluid sample.

11. The sensor of claim 10, further comprising a second partially reflective optical window disposed in the second optical pathway and configured to direct at least a portion of the light emitted from the first optical emitter toward a first reference optical detector.

12. The sensor of claim 10, wherein the optical emitter assembly is removably attached to the optical sensor in the first optical pathway between the first partially reflective optical window and the optical window.

13. A method comprising:
positioning an optical sensor in optical communication with a fluid sample under analysis, the optical sensor comprising:
a housing;
a first optical emitter;
a second optical emitter;
a first optical pathway defined by the housing;
an optical detector; and
an optical window supported by the housing and optically coupling the optical sensor and the fluid sample;
emitting light at a first wavelength by the first optical emitter through a first optical pathway and the optical window from the housing into the fluid sample;
detecting fluorescent emissions emitted by the fluid sample through the optical window and the first optical pathway by an optical detector;
emitting light at a second wavelength different than the first wavelength by a second optical emitter through the first optical pathway and into the fluid sample under analysis via the optical window, the second optical emitter being positioned in first optical pathway; and
detecting light scattered by the fluid sample through the optical window and the first optical pathway by the optical detector.

14. The method of claim 13, wherein emitting light at a first wavelength through the optical pathway comprises directing the light at the first wavelength into a second optical pathway intersecting the first optical pathway between the optical detector and the optical window at an approximately 90 degree angle.

15. The method of claim 14, wherein the optical sensor further comprises a partially reflective optical window disposed at the intersection of the first and second optical pathways, such that:
at least a portion of the light at the first wavelength directed into the second optical pathway is reflected by the partially reflective optical window into the first optical pathway and to the fluid sample; and
at least a portion of the light directed from the fluid sample through the optical window into the first optical pathways is transmitted through the partially reflective optical window to optical detector.

16. The method of claim 13, further comprising determining at least one characteristic of the fluid sample based on the detected fluorescent emissions from the sample.

17. The method of claim 16, wherein the at least one characteristic is a fluorophore concentration of the sample.

18. The method of claim 16, further comprising determining the turbidity of the fluid sample based on the detected light scattered by the fluid sample.

19. The method of claim 18, wherein determining the at least one characteristic of the fluid sample is further based on the determined turbidity of the fluid sample.

20. The method of claim 19, wherein the optical sensor further comprises a first reference optical detector configured to receive at least a portion of the light emitted from the first optical emitter and a second reference optical detector configured to receive at least a portion of the light emitted from the second optical emitter, and wherein determining the at least one characteristic of the fluid sample is further based on the detected light from the first reference optical detector and the detected light from the second reference optical detector.

21. The method of claim 20, wherein the optical sensor further comprises a removable optical emitter assembly, the removable optical emitter assembly comprising the second optical emitter and the second reference optical detector.

22. The method of claim 21, further comprising coupling the removable optical emitter assembly to the optical sensor proximate the first optical pathway.

23. The method of claim 20, further comprising:
comparing the detected light at the first optical detector and the detected light at the first reference optical detector to determine a relative fluorescence measurement; and
comparing the detected light at the second optical detector and the second reference optical detector to determine a relative turbidity measurement; wherein
determining at least one characteristic of the fluid sample based on the detected fluorescent emissions from the sample comprises combining the relative fluorescence measurement and the relative turbidity measurement.

24. The method of claim 20, wherein the first reference optical detector and the second reference optical detector are connected electrically in parallel to provide reference signals to the single electrical channel.

25. An optical sensor comprising:
a first optical pathway;
an optical window optically connected to the first optical pathway and configured to:
direct light from the first optical pathway into a fluid sample, and
receive light from the fluid sample through the optical window;
a second optical pathway intersecting the first optical pathway at an approximately 90 degree angle;
a first optical emitter coupled to the second optical pathway and configured to emit light at a first wavelength into the fluid sample via the second optical pathway, the first optical pathway, and the optical window; and
a second optical emitter configured to emit light at a second wavelength into the first optical pathway between the optical window and the intersection of the first optical pathway and a second optical pathway and toward the fluid sample.

* * * * *